United States Patent [19]

Charkoudian et al.

[11] Patent Number: 5,543,054
[45] Date of Patent: Aug. 6, 1996

[54] METHOD AND APPARATUS FOR COVALENT IMMOBILIZATION OF CHARGE- CONJUGATED CARBOHYDRATE MOLECULES

[75] Inventors: John Charkoudian, Carlisle; Malcolm Pluskal, Acton; David Wang, Lexington; Charles Phoebe, Uxbridge, all of Mass.

[73] Assignee: Millipore Corporation, Bedford, Mass.

[21] Appl. No.: 157,805

[22] Filed: Nov. 24, 1993

[51] Int. Cl.[6] .............................. B01D 61/38; C07H 1/06; G01N 27/26
[52] U.S. Cl. ............... 210/638; 210/500.36; 210/500.37; 210/500.41; 210/502.1; 210/506; 204/462; 436/94; 436/172; 436/178
[58] Field of Search ..................................... 210/506, 690, 210/692, 500.36, 500.37, 500.41, 502.1, 638, 645; 436/91, 93, 94, 172, 178; 204/182.3

[56] References Cited

U.S. PATENT DOCUMENTS

| | | | |
|---|---|---|---|
| 4,512,896 | 4/1985 | Gershoni | 210/635 |
| 4,617,124 | 10/1986 | Pall et al. | 210/638 |
| 4,778,601 | 10/1988 | Lopatin et al. | 210/500.27 |
| 5,004,543 | 4/1991 | Pluskal et al. | 210/490 |
| 5,019,231 | 5/1991 | Brandley et al. | 204/182.1 |
| 5,071,909 | 12/1991 | Pappin et al. | 525/54.1 |
| 5,087,337 | 2/1992 | Brandley et al. | 204/182.1 |
| 5,094,731 | 3/1992 | Brandley et al. | 204/182.1 |

FOREIGN PATENT DOCUMENTS

| | | | |
|---|---|---|---|
| 0421972 | 10/1991 | European Pat. Off. | C12Q 1/54 |
| 8810422 | 12/1988 | WIPO | G01N 27/26 |
| 9105265 | 4/1991 | WIPO | G01N 33/66 |
| 9219974 | 11/1992 | WIPO | 436/94 |

OTHER PUBLICATIONS

Bjerrum, Ole J., et al, Electrophoresis 8:388–397 (1987).
Church, George M., et al., PNAS (USA) 81: 1991–1995 (1984).
Demeulemester, Claude, et al., Electrophoresis 8: 71–73 (1987).
Edge, Cristopher, et al., Nature 358: 693–694 (1992).
Lee, K. B., et al., Anal. Biochem. 205: 108–114 (1992).
Lee, Kyung–Bok, et al., Carbohydrate Res. 214: 155–168 (1991).
Merkle, R. K. et al., Methods in Enzymology 138: 232–250 (1987).
Osawa, T., et al., Ann. Rev. Biochem. 56: 21–42 (1987).
Van de Sluis, P. J. et al., J. Immun. Methods 104: 65–71 (1987).

Primary Examiner—Robert A. Dawson
Assistant Examiner—Kenneth M. Jones
Attorney, Agent, or Firm—Andrew T. Karnakis

[57] ABSTRACT

A method for covalent immobilization of a carbohydrate molecule with an oppositely charged surface, comprising the steps of adsorbing the carbohydrate molecule to the oppositely charged surface in proximity to reactive moieties bound to the charged surface; and next activating the bound moiety sufficiently for covalent attachment to the adsorbed carbohydrate molecule. Also disclosed is a hydrophobic microporous polymer membrane coated with a cross-linked, cationic polymer having fixed charges thereon, the coating having enhanced epoxide content for covalent immobilization of the oppositely-charged carbohydrate molecule. A novel method for sequencing carbohydrates by covalent attachment of a carbohydrate conjugate to the membrane, and subsequent treatment with glycosidases, is also presented.

31 Claims, 9 Drawing Sheets

Figure 5 A
AMAC
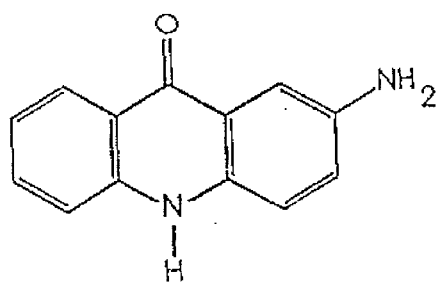
2-aminoacridone
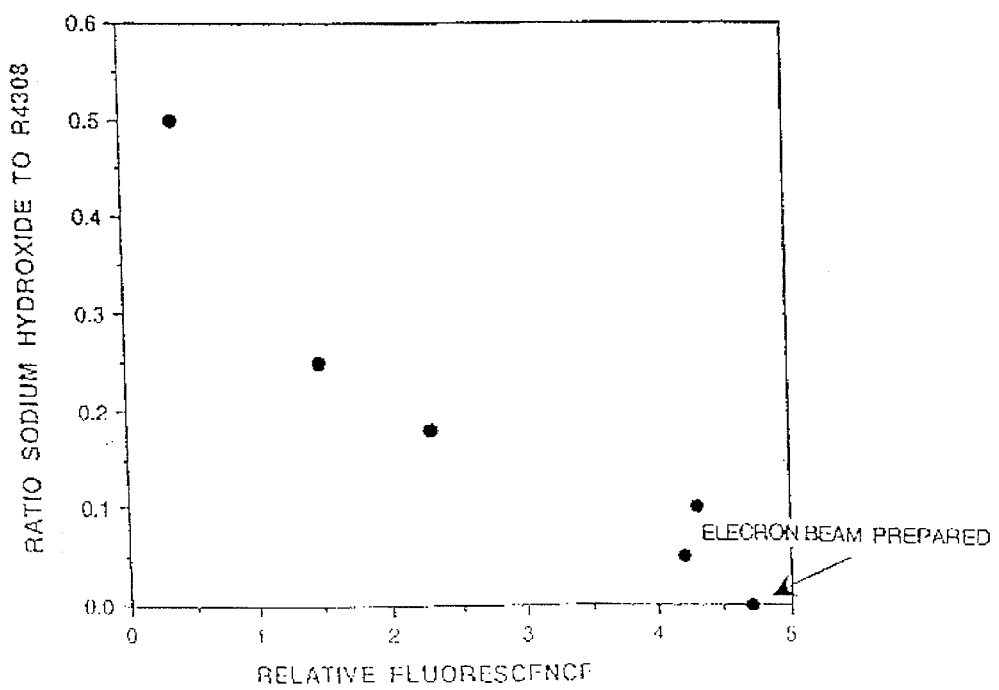
Figure 5 B

METHOD AND APPARATUS FOR COVALENT IMMOBILIZATION OF CHARGE- CONJUGATED CARBOHYDRATE MOLECULES

BACKGROUND

1. Field of the Invention

The present invention relates generally to the analysis of molecules. In particular, the invention is a novel immobilization technique and substrate wherein a normally electrically-neutral macromolecule is subjected to a chromatographic or electrophoretic separation in the form of a charged conjugate, followed by covalent attachment to a surface. The retained molecule may then be tested utilizing a variety of probing strategies employing specific bioaffinity molecules. More particularly, the invention relates to covalent immobilization of charge-conjugated carbohydrate molecules to a blotting membrane and subsequent determination of activity or structure.

2. Description of the Background Art

Immobilization of macromolecules on a solid-phase support matrix is a technique which has seen widespread use in affinity applications. Most affinity applications require that the molecule or ligand of interest react with the solid phase surface covalently. In most cases the solid phase surfaces are in the form of chromatographic supports, i.e., beads or particles. *Affinity Chromatography. A Practical Approach*, P. D. G. Dean, ed, IRL press. Porous membrane substrates have been reported, i.e., diazo activated cellulose (Alwine, J. C., Kemp, D. J. and Stark, G. R., *Proc. Natl. Acad SIC U.S.A.* 74:5350–5354 (1977)), Immobilon-AV™ (Millipore Corp., Bedford, Mass.) (Blankstein, L. A. et al., *Am. Clin. Prod. Rev.* 4:33–34 (1985), and activated nylon (Huse, K. et al., *J. Chromatography* 502:171–177 (1990). Non-covalent binding on nitrocellulose, or via ionic (nylon) or hydrophobic polyvinyldifluoride (PVDF) -based membrane mechanisms are reversible and may not retain the molecule or ligand of interest for the intended application. This can be a problem with small molecules such as peptides, oligonucleotides or oligosaccharides, or where competing ions may wash away the adsorbed ligand.

Covalent immobilization on several blotting surfaces is known. Examples include activated paper (TransBind™, Schleicher & Schuell Ltd., Keene, N.H. ) carbodimidazole-activated hydrogel-coated PVDF membrane (Immobilon-IAV™, Millipore Corp., Bedford, Mass.), activated nylon (BioDyne™, Pall Corp., (Glen Cove, N.Y.), DVS- and cyanogen bromide-activated nitrocellulose. Such surfaces are activated prior to transfer of the molecules from the electrophoresis gel and are reactive only if the molecule is well retained by the surface and sufficient "residence time" on the surface allows for reaction before the surface chemistry decays by hydrolysis or non-specific reaction with components of the electrophoresis system. While adsorbed in the dry state and kept in the dark, these blots are stable. Most applications of these blots, however, require further manipulation, often in aqueous buffer systems. These environments can lead to desorption of the blotted pattern, and thus information and material become lost. UV cross-linking of DNA (Church et al., PNAS 81:1991–1995(1984)) and RNA (Khandjian, et al., *Anal. Biochem.* 159:227–232 (1986) to nylon membranes is well known, and is thought to proceed via a thymidine radical initiated attack upon membrane primary amines.

U.S. Pat. No. 4,512,896 (Gershoni), Transfer of Macromolecules from a Chromatographic Substrate to an Immobilizing Matrix, discloses a charge-modified hydrophilic porous membrane used to immobilize blotted macromolecules. The preferred membrane material is nylon, and the surface is modified with Hercules R-4308 or Polycup 172, 2002, or 1884. The epoxide group is used to link the surface-modifying agent to the polymer surface, the usual method of binding the polymer coating to the membrane surface. No examples of permanent or covalent attachment of macromolecules are disclosed.

U.S. Pat. No. 5,004,543 (Pluskal et al.) discloses a cross-linked cationic charge-modifying polymer coating on a hydrophobic microporous polymer membrane substrate. The coating has fixed formal positive charge groups and halohydrin groups. The coated membrane is produced by contacting the membrane with an aqueous alkaline organic solution of the polymer Hercules R-4308. Again, no examples of macromolecule blotting are shown.

The blotting of modified carbohydrates to membranes is an area of active interest, as shown by the following discussion. A molecule or ligand successfully retained on a solid phase surface is available to form biospecific or affinity interaction with other macromolecules for the purposes of, for example, purification, chemical modification, or confirmation of biological activity. In the latter case the retained molecule or ligand is then subjected to testing techniques with various labeled protein compounds. Antibodies may be used to identify specific proteins. In the case of retained oligosaccharides or glycans released from a proteoglycan or other source molecule, lectins may be used to uniquely identify the adsorbed carbohydrate.

Determination of the sequence and structure of carbohydrates, specifically oligosaccharides, can be of significant importance in various fields, particularly in the medical and pharmaceutical fields. For example, the carbohydrate structure of a glycoprotein can have a significant effect upon its biological activity. That is, the oligosacchafides can affect the protein's antigenicity, stability, solubility and tertiary structure. The carbohydrate side-chains also can influence the protein's half-life and target it to receptors on the appropriate cells. The carbohydrate residues can affect both inter- and intra-cellular recognition. The sugar groups thus can control the relative effectiveness of a therapeutic protein when administrated to a patient. These and other such functions of the carbohydrate moiety of glycoproteins are discussed, for example, by Delente, *Trends in Biotech.* 3(9):218 (1985); van Brunt, *Bio/Technology* 4:835–839 (1986); and Taunton-Rigby, *Biotech USA 1988*, Proc. Conf. San Francisco, Nov. 14–16, pp. 168–176 (1988); and Varki, *Glycobiology* 3(2) 97–130 (1993).

Methods have also been developed for determining the sequence of oligosaccharides such as that described by Kobata in *The Carbohydrates of Glycoproteins, Biology of Carbohydrates*, (Ginsburg and Robins, Eds.), John Wiley and Sons, Vol. 2, pp. 87–162, (1984); Snider, ibid., pp. 163–193, 1984. See also Harada et al, *Anal. Biochem.* 164 374–381 (1987). Most proteins are glycoproteins which contain either O-gycosidically linked and/or N-gycosidically linked saccharides. These saccharides may vary from a single monosaccharide to highly branched structures containing over 30 monosaccharide residues. The determination of a monosaccharide sequence in such an oligosaccharide involves determining the order and branching pattern of the monosaccharide residues, the orientation of each glycosidic linkage ($\alpha$ or $\beta$) and the linkage between the various monosaccharides, i.e. 1→3, 1→4, etc.

Most of the available enzymatic techniques for sequencing oligosaccharides are sequential in nature, that is, a single reaction is performed and its products are analyzed, followed by a second reaction and a second analysis, performed either on the starting material or on the products of the first reaction. The sequential analyses methods usually rely on enzymatic analysis using exoglycosidases. These enzymes specifically cleave the non-reducing terminal monosaccharide of an oligosaccharide.

These sequential enzymatic techniques have the advantage of great flexibility and sensitivity. That is, each subsequent reaction can be selected on the basis of the previous results, and the products of one reaction can be used as the starting point for the next. However, there also are disadvantages in these techniques in that the process can be slow, being a sequential technique, and difficult to automate unless the procedure is predefined, thereby resulting in loss of its flexibility. Other methods of oligosaccharide structure elucidation include $H^1$-NMR, mass spectrometry, and sequential lectin chromatography.

A recent improvement in sequential saccharide analysis is found in European Patent application EPO 421972 (Rademacher), for a technique dubbed Reagent Array Analysis Method (RAAM). The central idea is that when an oligosaccharide is exposed to a specific reagent mix having an array of oligosaccharide-cleaving enzymes, normally all linkages but one will cleave. When a reagent mix lacking the specific linkage enzyme is contacted with the oligosaccharide, no cleaving occurs, indicating which linkage is present. This approach lends itself to automation to a significant degree. However, if the oligosacharide bond is cleaved by more than one enzyme, a non-specific signal results.

The transfer of carbohydrate-conjugates from an electrophoresis gel to a membrane-based solid phase has been described in U.S. Pat. Nos. 5,019,231, 5,087,337, and 5,094,731 as the first step of a blotting application. Charged conjugate derivatives of the released oligosaccharides were derived by Schiffs' base formation between amine-containing charged fluorescent molecules such as 1-amino-4-naphthalene sulfonic acid (ANSA), 1-amino-1,6-disulphonic acid (ANDA) or 8-aminonapthalene-1,3,6-trisulfonic acid (ANTS). These sulphonated aminonaphthalenes only differ in their degree of sulfonic acid substitution, which in turn determines their total amount of ionic charge. The '231 and '731 patents are directed to a method of separating and analyzing saccharides by reacting saccharides with ANSA ('231) or more broadly, charge-generating and fluorescing moieties ('731), separating the conjugates on a gel, electroblotting the conjugates onto a nylon membrane, and probing the membrane-bound saccharide conjugates. Binding to the membrane is apparently difficult, because the charged ANSA tag was deficient in holding the neutral oligo-saccharide, and a secondary polyisobutylene methylmethacrylate polymer matrix was used to overcoat the adsorbed conjugates to bring about the necessary retention.

The previously mentioned '337 patent is directed to a method for separating and detecting saccharides by first reacting saccharides with a tri-functional compound, electrophoresing them, electroblotting them onto a nylon membrane, and then activating the light-sensitive azido group of the conjugate, which allows covalent binding to the nylon membrane. The tri-functional compound is a modified ANSA having an azido group at the 5, 6, 7, or 8 positions. The conjugate is attached to the membrane through light-activation of an azido group on the ANSA molecule. However, here the molecule, not the membrane, is activated. Also, these molecules are very light sensitive and have short shelf-lives.

U.S. Pat. No. 5,205,917 (Klock) is directed to fluorophore-assisted carbohydrate electrophoresis (FACE) used in a method of medical diagnosis. ANTS-carbohydrate derivatives are electrophoresed and recorded via charge-coupled device detector (CCD), or electroblotted onto nylon or nitrocellulose membranes. ANTS-carbohydrate analyses of individuals with glycoconjugate metabolic diseases are compared against normal people. This method does not attempt or result in covalent immobilization, and is directed to identification of metabolic disorders by comparison of patterns of electrophoresed carbohydrates.

Patent Cooperation Publication Application No. WO 91/05265 (Jackson) is directed to the use of a polymer membrane to blot electrophoresed ANTS-carbohydrate conjugates which have been run on an electrophoresis gel. Immobilon-N™ (Millipore Corporation), a cationically-coated PVDF membrane, is used to electroblot PAGE-separated ANTS-labeled sugars. The adsorption mechanism is believed to be electrostatic.

The need for better covalent immobilization of macromolecules to blotting membranes is apparent. There remains a need for proven methods and matrices for flexible means of immobilizing carbohydrates for further analysis, including sequencing.

SUMMARY OF THE INVENTION

Applicants have developed a novel method and membrane for covalently binding modified carbohydrates to a membrane. The invention is directed to a method for covalent immobilization of a carbohydrate molecule with an oppositely charged surface, including the steps of adsorbing by ionic attraction the carbohydrate molecule to the oppositely charged surface in proximity to reactive moieties bound to the charged surface; and then activating the membrane-bound moiety sufficiently for covalent attachment to the adsorbed carbohydrate molecule. In the preferred embodiment, normally neutral carbohydrates are charged by covalent conjugation with a charged fluorophore, preferably sulfonated aminonaphthalene, particularly 8-aminonapthalene-1,3,6-trisulphonic acid (ANTS). The carbohydrate is a reducing oligosaccharide, and may be a glycan released from a glycoconjugate source. The oppositely-charged surface may be a porous polymer, particularly Polyvinylidene Fluoride (PVDF) or ultra-high molecular weight polyethylene (UPE), coated with a polyamido-polyamine epichlorohydrin resin, more particularly Hercules R-4308™. The charged surface may also be a non-porous surface such as a polymer film.

Another embodiment of the invention is a specially-prepared hydrophobic microporous polymer membrane coated with a cross-linked cationic polymer having fixed formal charge groups thereon, the coating having enhanced expoxide content for covalent immobilization of an oppositely-charged carbohydrate molecule, and having moieties for covalent immobilization of an oppositely carbohydrate molecule. In a preferred embodiment, the polymer membrane is UPE or PVDF coated with a polyamido-polyamine epichlorohydrin cationic resin, such as Hercules R-4308™. This results in the surface having cationic charge groups on it. The moieties are epichlorohydrin groups, from which are formed epoxide groups by the introduction of bases such as sodium or ammonium hydoxide. Special steps are taken during the membrane's manufacture to maximize the amount of epichlorohydrin present on its surface.

Another embodiment of the invention is a method for preparing the previously described polymer membrane, comprising the steps of contacting a hydrophobic microporous polymer membrane with an alkaline solution of a polymer of polyamido-polyamine epichlorohydrin, the solution having less than a stoichiometric amount of alkaline agent to enhance the epoxide potential of the membrane; then crosslinking the polymer by a combination of alkali and heat or electron-beam radiation; and lastly curing the membrane. Maximization of the epoxide potential of the coated membrane is achieved by using none (electron beam) or a stoichiometrically minimal amount of base such that epichlorohydrin content of the membrane is maximized.

A further embodiment of this invention is a method for determining the sequence-specific structure of a carbohydrate, comprising the steps of (a) releasing a carbohydrate from a carbohydrate source molecule whereby a free aldehydic carbohydrate is available; (b) conjugating the free aldehydic carbohydrate to a charge-bearing aminoflurophore; (c) transferring the conjugated carbohydrate to a hydrophobic microporous polymer membrane coated with a crosslinked, cationic polymer having fixed charges thereon, the coating having enhanced epoxide content for covalent immobilization of an oppositely-charged carbohydrate molecule; (d) activating the membrane thereby covalently immobilizing said adsorbed conjugated carbohydrate;(e) identifying a terminal or side-chain saccharide by subjecting the carbohydrate to an enzymatic identification procedure; and (f) repeating step (e) until a desired portion of the structure of the carbohydrate is determined.

Also a part of this invention is a kit for determining the structure of a carbohydrate, compartmentalized to receive in close confinement one or more containers which comprise in combination: (a) a hydrophobic microporous polymer membrane coated with a cross-linked, cationic polymer having fixed charges thereon, the coating having enhanced epoxide content for covalent immobilization of an oppositely-charged carbohydrate molecule; (b) a reaction vessel; (c) at least one charged aminofluorophore reagent; and d) enzymes for clipping carbohydrate molecules.

BRIEF DESCRIPTION OF THE FIGURES

FIG. 5A shows the structural formula of AMAC (2-aminoacridone), the primary amine used in FIG. 5B, a graph of base used in membrane manufacture vs. relative fluorescence.

DETAILED DESCRIPTION OF THE INVENTION

The invention is directed to a method for covalent immobilization of a carbohydrate molecule with an oppositely charged surface, comprising the steps of first adsorbing the carbohydrate molecule to the oppositely charged surface in proximity to reactive moieties bound to the charged surface; and then activating the moiety sufficiently for covalent attachment to the adsorbed carbohydrate molecule. The invention encompasses a broad scope of membranes, charge-carrying coatings, charge-bearing derivative molecules, and carbohydrate types.

Figure 1:
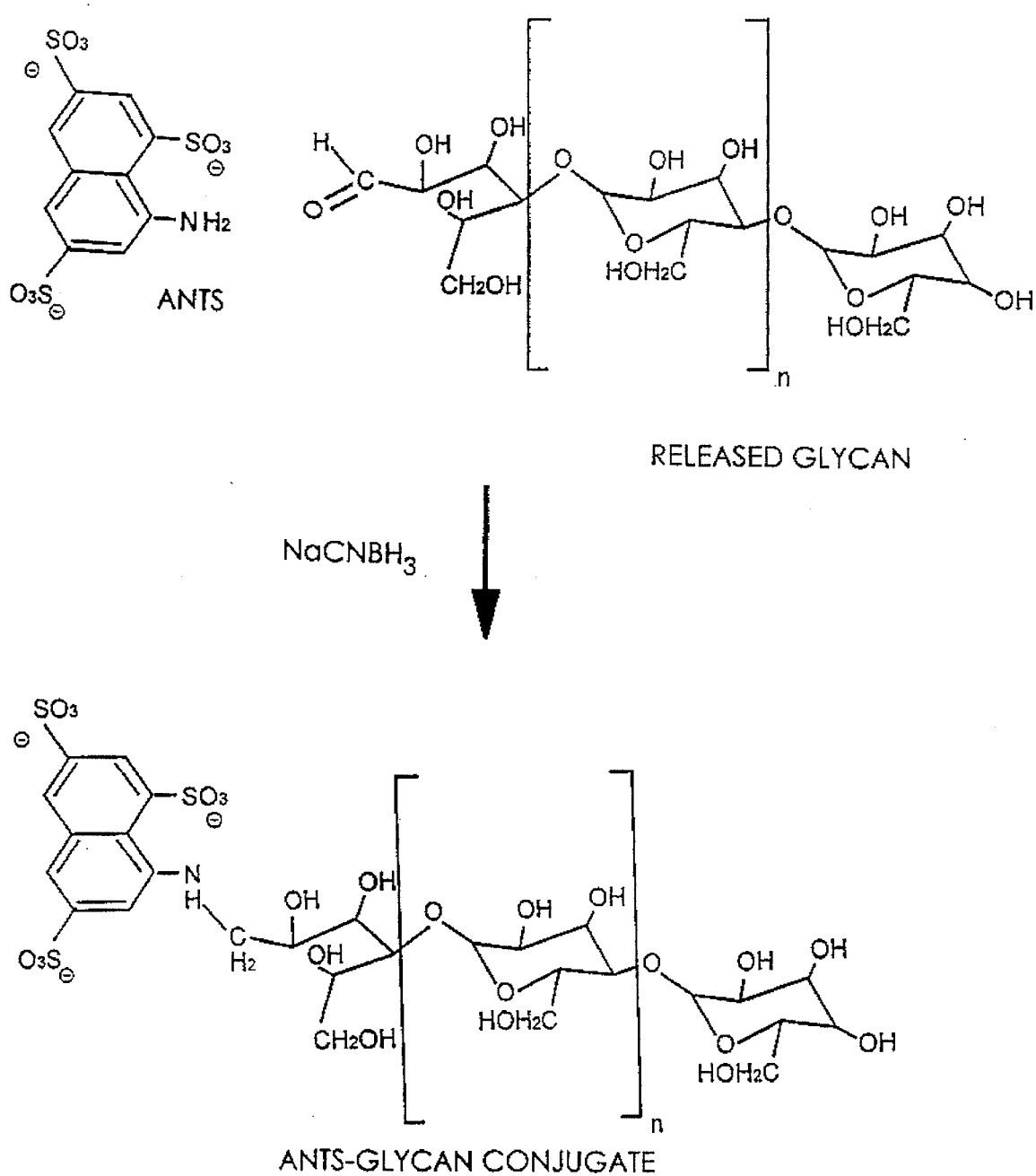
FIG. 1 is a schematic of the reactants of the invention involved in the carbohydrate-ANTS conjugation reaction pathway.

With particular attention to FIG. 1, the reactants of the preferred embodiment are depicted. Generally, an oligosaccharide molecule is shown in the top left corner, prior to derivatization. Oligosaccharides are polymers of monosaccharides, typically joined through their 1- or 4-hydroxyl groups, as shown. The oligosaccharide shown may have been released from some source molecule such as a proteoglycan. The top fight corner of FIG. 1 depicts the most preferred charge-beating derivative molecule of this invention, which is from the sulfonated aminonaphthalene class of fluorophores. ANTS (8-aminonaphthalene-1,3,6-trisulphonic acid) reacts with the released oligosaccharide in the presence of the reducing agent sodium cyanoborohydride to reductively aminate the terminal saccharide, leading to the ANTS-glycan conjugate shown in the lower portion of FIG. 1.

Figure 2:
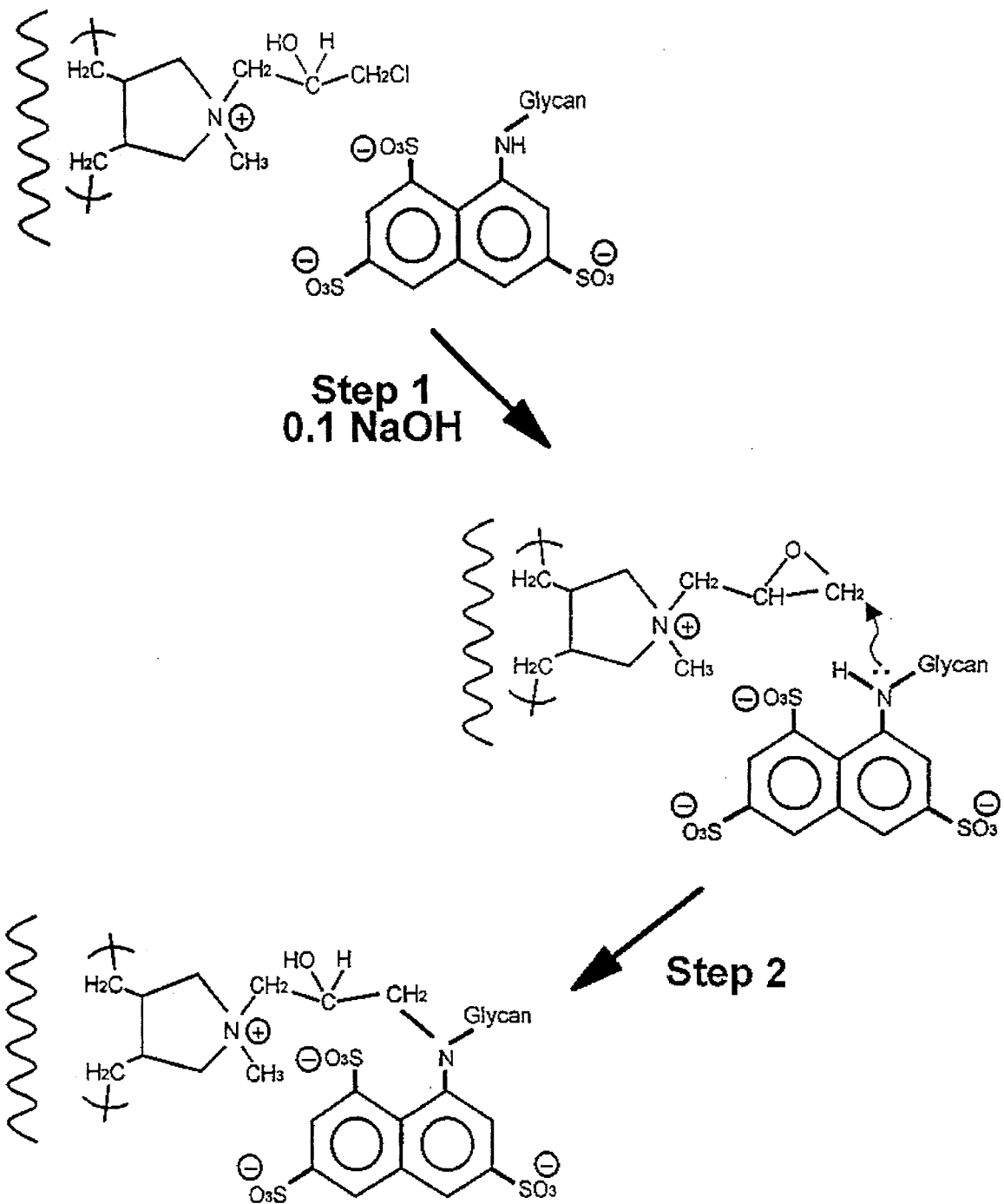
FIG. 2 is a schematic representation of a proposed theoretical reaction pathway of the covalent immobilization of the charge-conjugated carbohydrate to the membrane of the invention.

The invention encompasses two main steps, adsorption and activation, both of which cover a broad range of interactions, but which together form a specific sequence of events. Not wishing to be bound by any particular theory of the invention, the following may explain the observed mechanism. With particular attention to FIG. 2, the membrane (left) is coated with Hercules R-4308 polymer, some of which contains a positively-charged amido-chlorohydrin moiety (depicted). In the first step depicted on the left side, the oppositely charged carbohydrate molecules [ANTS-glycan conjugate (3⁻)], and quaternary ammonium (1⁺) are given the opportunity to contact one another, and in so doing they adhere to each other by an electrostatic or ionic mechanism. This mechanism is believed to be responsible for temporarily attaching the ANTS-glycan conjugate molecules to the substrate surface. Being noncovalent, however, the ions are dissociable, and will separate to some degree in the presence of competing polar and electrostatic forces. It is presently believed that it is this electrostatic association that brings the adsorbed species into extremely close contact. Other attractive forces may contribute to this adsorption, including hydrophobic interactions. Any chemical reaction producing a covalent bond between these molecules will proceed at its fastest and most efficient rate due to this spatial arrangement, because the rate of a chemical reaction depends on, among other things, the frequency of collisions with the proper steric orientation, and the concentration of the reactants, to produce the chemical reaction. Both factors are optimized due to the electrostatic association: the reacting functionalities are in close proximity and the local concentration of reactants is extremely high.

It is presently believed that the activation mechanism proceeds as follows: The activation of the surface moiety is depicted by the arrow. When base, in this instance 0.1M NaOH, is allowed to permeate the membrane, the epichlorohydrin moiety internally cyclizes to form a very reactive three-membered cyclic epoxide moiety:

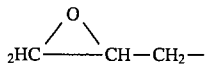

This epoxide contains an electrophilic methylene group, which may be attacked by the very closely-located amine. Step 2 depicts the final product of this base-catalyzed nucleophilic attack the glycan-ANTS-quaternary ammonium complex.

While alkalinity clearly affects the speed of the reaction, the temperature of the membrane during the immobilization reaction also affects it. For instance, immobilization using 0.1M NaOH occurs in 15 minutes at 50° C., as compared to one hour at 24° C. Decreasing alkalinity to 0.01M NaOH at 24° C. extends the time necessary for immobilization to 48 hours instead of one hour at 0.1M. In fact, some immobilization can occur in deionized water if temperatures are elevated (70° C.) for long enough times, such as 96 hours. Thus, a combination of alkalinity and temperature may be selected to optimize the derivatization without undue experimentation, given these teachings.

The method of the present invention is especially useful for subsequent manipulations of the oligosaccharide, including identification, sequencing, and probing with lectins or antibodies.

Many biomolecules are charged at physiological pH's. DNA has a negative charge, while peptides and proteins may have either charge depending on their isoelectric point. If a biomolecule is uncharged, charge can be conferred to the molecule by conjugation to a charged material. In the case of the carbohydrate species for which examples are given here, the carbohydrate is linked to a negatively charged fluorescent chromophore by a standard reductive amination coupling reaction.

As previously described but now presented in more detail, the first step of the preferred embodiment involves conjugating the normally-neutral oligosaccharide molecules to a carbohydrate molecule. This is done in order to allow the individual saccharides to be separated from each other by electrophoretic techniques, which require that the materials being separated be charged. Any charged compound that also bears a nucleophile may be used for subsequent nucleophilic attack upon the activated membrane. It is also useful if the charged compound is fluorescent so that it may be visualized in the gel or upon the membrane during and after electrophoresis. Depending upon the type of saccharide, aminonapthalenes are a preferred group of such compounds. There are at least three closely related species. If one —SO₃=group is present upon the aminonaphthalene ring system, the compound is 1-amino-4-naphthalenesulfonic acid ("ANSA"). If two are present, the molecule is referred to as ANDA (1-aminonaphthalene-6, 8 -disulphonic acid, and three such groups ("ANTS") is 8-aminonapthalene-1,3, 6-trisulfonic acid. The most preferred is ANTS, because it has the highest charge density, thus binding the tightest to the membrane and conferring the highest charge-to-mass ratio of the three.

It will be understood by one of ordinary skill in the art that two molecules, each bearing one of the necessary functionalities (charge, nucleophilicity), may be individually attached to the oligosaccharide molecule. However, for the sake of convenience, bifunctional molecules such as those reported herein are preferred.

The ANTS molecule used in connection with the present invention has the following structural formula:

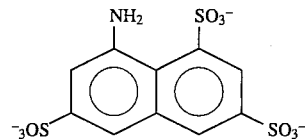

The —NH₂ amino group is indicated as being in the "8" position and the three —SO₃ groups are at the 1, 3, and 6 positions of the napthalene molecule. The shared double bonds in each ring structure provides the fluorescent character when ANTS conjugates are exposed to U.V. light.

Other aminoflurophores also come within the scope of the invention. For instance, Lucifer Yellow CH is a hydrazide-group-containing fluorophore that may be conjugated to oligosaccharides and electrophoresed, as reported in PCT Application No. PCT/US91/04555. Other bifunctional moieties capable of providing a charge and fluorescing when exposed to U.V. radiation are listed in U.S. Pat. No. 5,094,731 (Brandley, et al.), and incorporated herein by reference.

Conjugation of the oligosaccharide to the ANTS molecule is by way of a well-characterized Schiff's Base intermediate. A reducing reagent such as sodium cyanoborohydride (NaCNBH₃) is used to stabilize this reversible, reactive intermediate. As seen in FIG. 1, an oligosaccharide such as the released glycan shown can be conjugated to the ANTS molecule. The resulting ANTS-glycan may be run on an electrophoric gel to separate it from other similar ANTS-glycans that may be present. Purification of the ANTS mixture may be necessary in order to separate the ANTS compound from the conjugates. Since the reaction is run with an excess of ANTS, removal of ANTS is indicated in order to allow proper electrophoresis. The use of reverse-phase HPLC has been successful.

After the oligosaccharide/ANTS conjugates are formed, they are subjected to standard electrophoretic techniques in robe or slab gel formats or in capillaries in order to resolve the different oligosaccharides from each other. See "Gel electrophoresis of proteins,: a practical approach," Hames etal, eds. IRL Press. Examples of systems from which resolved carbohydrate-ANTS conjugates can be transferred to solid phases include polyacrylamide gels, agarose gels, and solution-filled membranes. A good example of the former systems are the PAGE gels where ANTS conjugates of carbohydrates are separated from their mixtures by electrophoresis. These gels display fluorescent band patterns reflecting the electrophoretic mobility of distinct conjugate species. Placing these gels against the membrane surfaces described above will result in transfer of the conjugate species to the membrane in the same band pattern originally displayed in the gel. One such procedure involves electroblotting. This type of transfer procedure involves transferring the resolved bands within the gel to a support matrix such as a nitrocellulose sheet. The transfer is carried out by the application of an electric field transverse to the original separation path and therefore is distinguishable from a more conventional alternative which involves the capillary transfer of such materials through Southern and Northern blotting.

Figure 3:
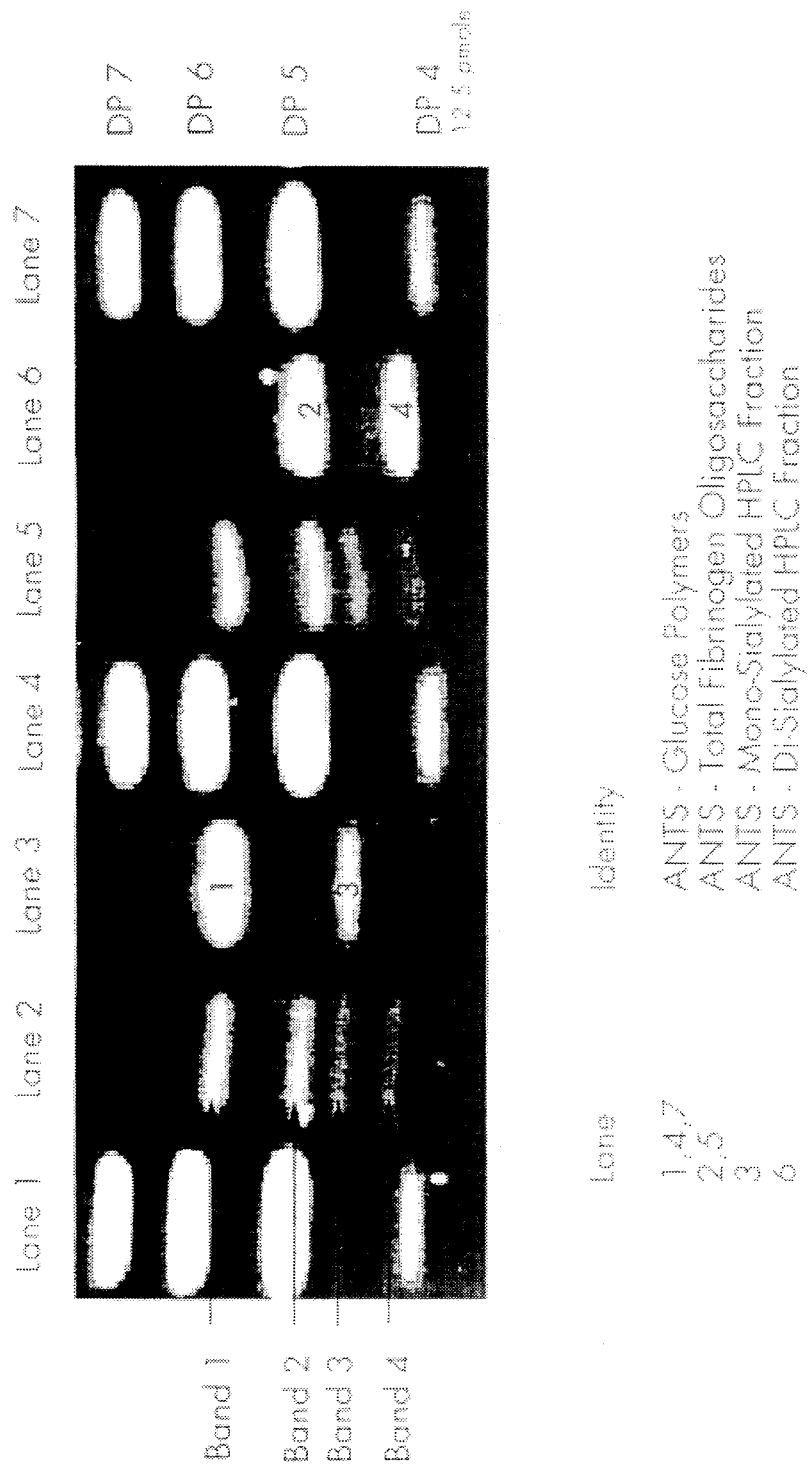
FIG. 3 is a photo of a gel wherein the conjugated oligosaccharides are separated from each other in different bands along the length of the gel. A Wheat Starch Ladder is separated in lanes 1, 4 and 7. Fibrinogen, a glycoprotein having four different oliogosaccharides, is separated in lanes 2 and 5. Mono- and di-sialated fractions from lane 2 are shown in lanes 3 and 6, respectively.
Figure 4:
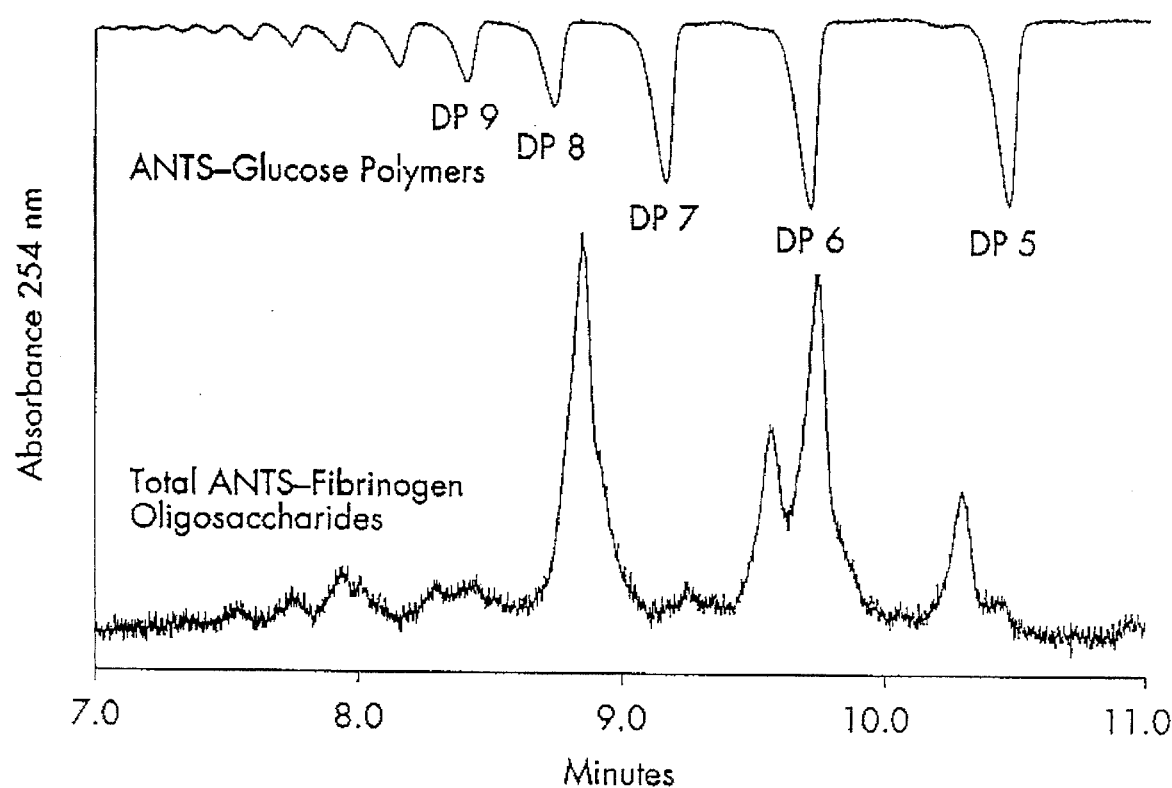
FIG. 4 is a capillary electrophoretogram of absorbance versus minutes for a run separatingwheat-starch ladder polymers and Fibrinagen-derived aligosaccharides. Total ANTS-fibrinogen oligosaccharides are shown in the lower trace, and ANTS-glucose polymers are shown in the upper trace.
Figure 6A:
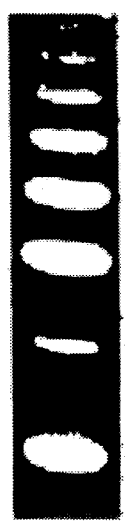
FIG. 6 is a resolved fluorescent band pattern. Panel A is a gel containing a wheat starch hydrolysate, clearly resolved into a series of bands of increasing polymer size. Panel B is a piece of ultrahigh molecular weight polyethylene (UPE) coated with R-4308, showing that the bands are transferred from the gel of Panel A to the membrane surface of Panel B by passive diffusion. Panel C is a photograph of the gel showing no fluorescence remaining in the gel after transfer. Panels D and E, D being having been treated with water (control) and E activated with base (test), show that the control and test pieces have the same fluorescent band pattern as they had before their respective treatments. Panels F and G are the same membranes as Panels D and E after washing with 2% aqueous NaCl salt solution for 2 hours. Panel F shows the washing off of the adsorbed wheat starch conjugates.
Figure 6B:
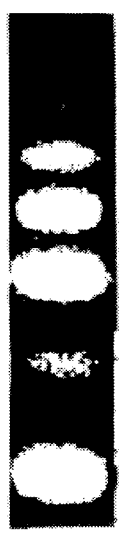
Figure 6C:
Figure 6D:
Figure 6E:
Figure 6F:
Figure 6G:

As depicted in FIG. 3, the slab gel separation of three distinct classes of oligosaccharides is shown. The electrophoretic resolution preferably utilizes a gel wherein the conjugated oligosaccharides are separated from each other in different bands along the length of the gel. A Wheat Starch Ladder is separated in lanes 1, 4 and 7. Fibrinogen, a glycoprotein having four different oliogosaccharides, is separated in lanes 2 and 5. Mono- and di-sialated fractions from lane 2 are shown in lanes 3 and 6, respectively. In FIG. 4 an example is depicted for the separation of the same classes of ANTS oligasaccharide conjugates by capillary electrophoresis. This pattern shows a similar resolution of total ANTS-fibringen oligasaccharides (see FIG. 3, lanes 2 and 5) as seen in the slab gel format.

The carbohydrates suitable for the method of the present invention represent a wide range of reducing carbohydrate structures including simple linear oligomers of glucose to complex branched oligosaccharides obtained from the enzymatic or chemical deglycosylation of glycoconjugates. The invention is applicable to use on a diversity of carbohydrate structures, including those derived from glycoproteins, proteoglycans, glycolipids, glycosphingolipids, polysaccharides, glycosaminoglycans and other biomolecules, including complex biomolecules containing any of these as a component.

The negatively-charged conjugates may be adsorbed onto substrate surfaces having a positive charge. For example, membranes having a surface coating of polyaminoethylmethacrylate hydrochloride will act as an electrostatically attractive substrate, and will attract ANTS-glycan conjugates from gel to give adsorbed blots having a fluorescent image. In addition, the polymer polyethyleneimine when sufficiently cross-linked will place quaternary ammoniums on the surface (See U.S. Pat. No. 5,071,909). MAPTAC, discussed infra, is a monomer which may be used to attach quaternary ammoniums to a membrane The invention also is more broadly directed to oppositely-charged surfaces. For instance, if a positively-charged moiety were attached to a carbohydrate, it would be attracted to a negatively-charged surface such as Polyacrylic acid, which functions to place negative charges (COO—) on the surface. Other membrane surface charge-carrying modifiers not listed here also come within the scope of this invention.

A variety of membranes and materials may be coated with any charge-bearing polymers and thereby come within the scope of this invention. Plastics (polytetrafluroethylene, polyvinylidene fluoride, polyester, polycarbonate, polypropylene, polymethylmethacrylate, polymethacrylate, polysulphone, or polystyrene), glass, ceramics, metals, zeolites, silica, or alumina are some of the materials. Microporous polymer membranes are a preferred substrate for this invention. Hydrophobic, microporous polymer membranes are particularly preferred. It has been found that hydrophilic membranes are not especially indicated for practice in the present invention.

2. Membrane

The invention is also directed to a novel membrane that is optimized for this covalent blotting method. There are many porous substrates which can provide the underivatized surface for the adsorption step, and these include membranes, resinous beads and chromatography particles. The principal limitations are 1) that the surface have fixed charge groups opposite in polarity to that of the charged conjugate, and 2) that the surfaces have chemical moieties in reactive proximity to the bound charged conjugate. Although positively- and negatively-charged surfaces may in theory be used, cationic-charged surfaces are presently preferred. Commercial products with a cationic polymer surface include Millipore Corporation's Immobilon-N™ (Bedford, Mass.). Zetabind® (Cuno Corp., Meriden, Conn.), GeneScreen® (NEN/DuPont, Boston, Mass.), and Posidyne® (Pall Corp., Glen Cove, N.Y.) are also R-4308™ coated membranes. However, not all of these surfaces are guaranteed to react to give covalent immobilization because the epichlorohydrins from the original R-4308 coating are exhaustively cross-linked with diamines, thereby extinguishing epoxide potential. Neutralizing the epichlorohydrins by the above cross-linking process on the membrane coating is practiced in most prior art membranes of this type. A typical process is disclosed in U.S. Pat. No. 4,473,474 (Ostreicher)(incorporated herein by reference), wherein the membrane is reacted with tetraethylenepentamine to cross-link R-4308™ polymer, thereby inactivating all remaining epichlorohydrins. Thus, surfaces having the capacity to permanently immobilize the absorbed species must be provided by special means.

Hercules Corporation (Wilmington, Del.) markets several polymers which have the capacity, when properly chemically manipulated, to provide both the positively-charged surface and the electrophile for covalent bond formation. These include the R-4308™ series of polyamido polymers and the POLYCUPS series of cationic resins (Polycup 172, 1884, 2002 or S2064). Other sources of polyamidopolyamine epichlorohydrin cationic resins are Cascamide Resin PR- 420 (Borden) and Nopcobond 35 (Nopco). These polymers may be coated on a variety of porous and nonporous substrates, and have the capacity to form highly active electrophilic moieties in their structures. U.S. Pat. No. 5,004,543 (Pluskal et al.) describes methods and materials for making Immobilon-N™, a microporous hydrophobic membrane having fixed cationic charge groups on its surface derived from the R-4308 polymer (Immobilon-N™ is available from and a trademark of Millipore Corp., Bedford, Mass.).

Surfaces can also be made from acrylate monomers having both positive charge and electrophilic characteristics. For example, copolymers of [3- (methacryloylamino)propyl] trimethylammonium chloride (MAPTAC) and glycidyl acrylate may be polymerized using thermal, UV, or electron beam methods, and homopolymer combinations of these and similar polymers are additional examples of suitable materials. Alternatively each monomer can be attached to the membrane surface sequentially using these energy sources. Cross-linkers can be included to enhance stability to heat and the chemical environment. These procedures are disclosed in U.S. Pat. Nos. 4,618,533 and 4,944,879 incorporated herein by reference.

The substrate membranes whose surfaces can be modified using these polymers typically include, but are not limited to, those made from polyvinylidene fluoride (PVDF), ultra-high molecular weight polyethylene (UPE), polytetrafluoroethylene (PTFE), and nylon (if not R-4308 coated and cross-linked with diamines). Hydrophobic surfaces are preferred. A commercially-available membrane suitable for use in this invention is the Immobilon-N™ Transfer Membrane (Millipore Corp., Bedford, Mass.) a charge-modified hydrophobic polyvinylidene fluoride membrane. A particularly preferred membrane material is UPE. UPE has a low fluorescence background, and when coated with R-4308™ polymer binds negatively-charged carbohydrate molecules tightly.

Manufacturing methods for coating membranes with charge-modifying polymers are disclosed in U.S. Pat. No. 5,004,543 (Pluskal et al.), incorporated herein by reference. A method for making membranes of UPE is disclosed in U.S. Pat. No. 4,778,601 (Lopatin et al.), also incorporated herein by reference. PVDF membranes are known in the art, and are described in U.S. Pat. Nos. 4,203,848 and 4,203,847, both of Grandine, 2d, and incorporated herein by reference.

An important aspect of the membrane used to covalently immobilize the charged conjugate molecule is its epoxide potential. This term refers to the amount of epichlorohydrin groups that remain on the surface of the R-4308™-coated membrane after it has been cured, but before the activation step. Most prior art processes teach the opposite, i.e., neutralizing the epichlorohydrins by chemical cross-linking with diamines, as discussed above.

Therefore, one theory of the invention teaches that a requirement of the membrane is that there be sufficient epichlorohydrins present on the surface for subsequent activation by base to the activated cyclic epoxide form. The term "epichlorohydrins" as used herein when referring to R-4308-coated membranes is synonymous with "epoxide potential," and may be used interchangeably throughout. In the R-4308 coating process, alkali is necessary to cross-link the epichlorohydrins to the membrane surface. The epoxide potential requirement is satisfied if less than a stiochiometric amount of base is used during the R-4308-coating step of the membrane, thereby decreasing the amount of cross-linking to the membrane, but maximizing the amount of epoxide potential left in the membrane. A "stoichiometric amount" of base is that amount required to convert all epichlorohydrins to epoxides. For a 20% solution of R-4308 polymer, that ratio is 0.25 (NaOH):1.0 (R-4308) on a weight-to-weight basis. A useful range of base to R-4308 is from about 0.20 to about 0.05. The most preferred ratio is 0.1/1.0. Use of lesser and lesser amounts of alkali in the manufacture process results in more epoxide potential. (See Tables 1 & 2, pages 25 and 26, and FIG. 5b). The only limitation is that as the alkali amount decreases, cross-linking to the membrane may decrease. One of ordinary skill will be able to determine when too little alkali results in insufficient cross-linking, as the coating will begin to slough off.

A novel epoxide potential assay is described in Example 2. It allows one of ordinary skill to determine the extent of epoxide density in a membrane made by the particular procedure being used, Generally, the procedure involves attaching the primary amine fluorophore 2-aminoacridone (AMAC), the structural formula shown in FIG. 5(A), which is an uncharged fluorescent primary amine, to the epoxides present on the activated membrane. Reaction between AMAC and surface epoxides occurs quantitatively, allowing an estimation of surface epoxide potential (epichlorohydrin content) by measuring bound AMAC fluorescence at 520 nm. FIG. 5(B) is a graph of fluorescence intensity versus the relative amount of sodium hydroxide used to cross-link the R-4308™ polymer, clearly showing that with less alkalinity, there is an increase in fluorescence due to AMAC bound through epoxide linkage to the membrane surface.

In an alternative embodiment, an electron beam is used to cross-link. The use of an electron beam to cross-link polymers is known, but its use to prepare R-4308-coated membranes for high epoxide potential as illustrated here is novel. FIG. 5(B) shows the effect of the use of an electron beam-it is represented by the point of highest relative fluorescence on the graph, indicating the highest number of epoxides present on the membrane.

3. Probing

For many applications covalent attachment is not, in itself, sufficient for further structural manipulation of the permanently immobilized biomolecule. The biomolecule's structure must be unaltered and accessible to probing reagents such that there is no hindrance to recognition. If the biomolecules' structure is altered by the immobilization chemistry, subsequent analysis could yield erroneous information. Detailed structural analysis of the biomolecule not only requires chemically resilient attachment, but also an environment where the biomolecule is freely accessible to reagents, some of which may be very large biomacromolecules, such as those represented by lectins or antibodies. Thus for the analysis of oligosaccharides derived from glycoconjugates, a group of proteins called lectins are used in an association reaction very similar to antibody-antigen reactions. The lectin, which is analogous to the antibody, must be unencumbered in its approach and interaction with the immobilized carbohydrate so that it can recognize its specific structural features. An example of lectin probing to identify a covalently-attached ANTS-glycan is shown in examples 4 and 5.

Lectins useful in the present invention encompass all lectins that are or may be used to specifically bind to any mono-, oligo-, or polysaccharide. These include, but are not limited to, Concanavalin A (from *Canavalia ensiformis*:specific for side chains containing terminal α-D-Mannose; *Aleuria aurantia* (specific for fucose α-1,6 linked to N-acetylglucosamine) lectin; *Amaranthus caudatus* (α anomers of NeuAc-Gal(β-1-3)-GalNAc, Gal(β-1-3-GalNAc bound to Ser/Thr; *Datura stramonium* (side chains containing β1,4-inked oligomers of N-acetylglucosamine or N-acetylylactosamine; *Galanthus nivalis* (side chains containing terminal mannose); *Helix pomatia* (α-D-GalNAc>α-D-GlcNAcα-DGal), *Lens culinaris* (α-D-Man>α-D-Glc>α-D-GlcNAc); *Maakia amurensis* (side chains containing SAα2→3Gal); peanut lectin (specific for side chains containing terminal Galβ→3GalNAc); *Phytolacca americana* (Pokeweed mitogen: specific for di-N-acetylchitobiose); *Ricmus communis* (terminal β-DGal); Soybean lectin (α-D-GalNAc>β-D-GalNAc>>α-D-Gal); Elder bark lectin (side chains containing either Neu5Acα2→6Gal or Neu5Acα2→6GalNAc); *Ulex europaeus* (α-L-Fucose); and wheat germ agglutinin (side chains containing terminal β-D-GlcNAc). These lectins are available commercially labeled with digoxigenin or biotin (Boehringer Mannheim, Indianappolis, Ind.).

The lectin probe can be directly labeled in such a way that the lectin-carbohydrate hybrid is directly detectable. These methods are well known, and include radiolabeling, chemiluminescent labeling, fluorometric labeling, chromophoric labeling, and antibody binding. Detection can be achieved by directly labeling the lectin with a ligand as, for example, biotin, which specifically binds to the protein streptavidin, and that protein can be a carrier for a chemiluminescent reaction component, as for example streptavidin linked covalently to alkaline phosphatase or horseradish peroxidase. All of these methods are well-known to one of ordinary skill in the art, and render the lectin detectably labeled.

Examples of antibody detection include the anti-digoxigenin enzyme-linked antibodies which localize to the digoxigenin-labeled lectin probe, and generate a purplish concentrate upon reaction with X-phosphate/NBT. One of ordinary skill will appreciate that other enzymes may be coupled to the bound antibodies for purposes of detection, including horseradish peroxidase and glutaraldehyde, and corresponding color-developing reagents applied. Specifically, the chemiluminescent reagent "LUMI-PHOS 530®", LumiGen, Inc., Detroit, Mich., allows the detection of lectin-carbohydrate hybrids on conventional X-ray film. Alternatively, other antidigoxigenin conjugates that would be suggested to one of ordinary skill include the fluorescers anti-digoxigenin-rhodamine, and anti-digoxigenin-fluorescein; and for electron microscopy anti-digoxigenin-(second antibody conjugated to gold).

Direct radiolabeling of the lectin-carbohydrate hybrid of the present invention is possible by radioiodination or reductive amination. See "Radioisotopes in Biology: a practical approach," Slater, R. J., er., IRL Press. Those of ordinary skill in the art will appreciate that other radioactive labels such as $^3$H or other radionuclides are also possible. Once the probes are labeled radioactively, detection is accomplished by exposure to X-ray sensitive photographic film. Subsequent development of the film will enable one to visually detect the presence or absence of hybridization. These methods are well-known to those of ordinary skill in the art.

Enzyme-linked immunoassay (ELISA) is another technique useful for detecting the lectin-carbohydrate hybrid of the present invention. The lectin reagent used in the present invention is principally characterized by its ability to bind to the saccharide side-chain or terminal saccharide through recognition of a specific sugar and linkage. Once the probe molecule is bound to a specific saccharide sequence, it can be detected by an antibody reagent. The antibody reagent can consist of whole antibodies, antibody fragments, polyfunctional antibody aggregates, monoclonal antibodies, single-chain antigen-binding molecules, or in general any substance comprising one or more specific binding sites from an anti-lectin antibody. When in the form of whole antibody, it can belong to any of the classes and subclasses of known immunoglobulins, e.g., IgG, IgM, and so forth. Any fragment of any such antibody which retains specific binding affinity for the bound probe can also be employed, for instance, the fragments of IgG conventionally known as Fab, F(ab'), and F(ab') $_2$. In addition, aggregates, polymers, derivatives and conjugates of immunoglobulins or their fragments can be used where appropriate.

The immunoglobulin source for the antibody reagent can be obtained in any available manner such as conventional antiserum, monoclonal antibody techniques, and recombinant genetic engineering of single-chain antigen-binding molecules. Antiserum can be obtained by well-established techniques involving immunization of an animal, such as a mouse, rabbit, guinea pig, sheep or goat, with an appropriate immunogen. The immunoglobulins can also be obtained by somatic cell hybridization techniques, such resulting in what are commonly referred to as monoclonal antibodies, also involving the use of an appropriate immunogen. Single-chain antigens are recombinantly engineered by insertion of a DNA segment coding for a linker polypeptide into a plasmid such that the linker will be expressed linking the two antigen-binding variable domains.

When the antibody reagent is used to detect hybrids, it will usually be labeled with an enzyme such as alkaline phosphatase, horseradish peroxidase, or glutaraldehyde, attached by suitable synthetic means. Alternatively, the antibody reagent can be detected based on a native property such as its own antigenicity. Further, antibody can be detected by complement fixation or the use of labeled protein A, as well as other techniques known in the art for detecting antibodies.

In a preferred embodiment the antibody reagent is labeled. The labeling moiety and the antibody reagent are associated or linked to one another by direct chemical linkage such as involving covalent bonds, or by indirect linkage such as by incorporation of the label in a microcapsule or liposome which is in turn linked to the antibody. Labeling techniques are well-known in the an and any convenient method can be used in the present invention.

The use of chromophoric labels on lectins can be detected by sight or by conventional means, such as by a light microscope. Recordation is by conventional color microphotography. Fluorescent or chemiluminescent labels emit light that may be detected by sight or by photomultiplier tube. Gold-conjugated labeling is used in electron microscopy to detect hybridization and to image the larger morphological features of the infected cell. Radiolabeled probes may be exposed to X-ray sensitive film.

4. Carbohydrate Sequencing

Attached to some of the asparagine and/or serine/threonine residues of most proteins are a complex mixture of oligosaccharides. These oligosaccharides are released from the protein either by chemical or enzymatic treatment. Once released the oligosaccharides can be "mapped" or "fingerprinted" by a number of analytical techniques including HPLC, IC, CE and PAGE. The mapping reveals the number and quantity of oligosaccharides present, but does not reveal the chemical structure or sequence of the oligosaccharides. In order to determine the chemical structure, the mixture of oligosaccharides must be submitted to a purification process (such as HPLC) which will result in a homogenous oligosaccharide. Classical techniques of structure elucidation (mass spectrometry and nmr) have been used to determine the structure of homogenous oligsaccharides, and have been referred to in the Background, supra.

Another means of determining the structure of a purified oligosaccharide is to submit it to a series of enzymatic digestions in which each digestion removes a specific monosaccharide linked in a specific manner. The use of enzymatic digestion sequencing, unlike traditional structure elucidation techniques, requires less material in order to determine the structure. However, the enzymes used in the sequencing process must be of the highest purity and have well characterized specificities. Such enzymes are now being recombinantly produced and can be commercially purchased. One such source is Glyko, Inc., Novato, Calif. The problem remaining in the process of enzymatic sequencing is the quantitative transfer of the oligosaccharide through the various enzymatic digestions. This can be accomplished by the covalent immobilaztion of the oligosaccharide onto a membrane, as taught herein. For example, an oligosaccharide mixture can first be labeled with ANTS or other suitable charge-carrying compound, and then purified by HPLC, IC, CE or PAGE as previously described. In the preferred embodiment, PAGE is used. Separated ANTS-oligosaccharides can be collected directly onto a membrane and the ANTS-oligosaccharide bands can be blotted onto the membrane from the polyacrylamide gels. Covalent immobilization is then carried out as discussed throughout. Once a selected group of enzymes have been used to treat the membrane, the resulting filtrates containing the released monosaccharides can be quantitatively analyzed. By knowing the enzyme specificities and the quantitative results a structure of the isolated oligosaccharide can be proposed.

Example 6 provides a detailed procedure for accomplishing oligasaccharide sequencing according to the foregoing rationale.

Having now generally described this invention, the same will become better understood by reference to certain specific examples which are included herein for purposes of illustration only and are not intended to be limiting unless otherwise specified. All U.S. patents cited herein are fully incorporated by reference in their entirety.

EXAMPLES

Example 1-Preparation of Epoxide-containing Membranes a. Solution Preparation:

A 3% solution of Hercules Corp. (Wilmington, Del.) R-4308 polymer in water with the desired level of NaOH is made by mixing stock R-4308 (20% solution) into water and adding slowly the desired amount of 5.0M NaOH to achieve the preferred ratio of 0.1 base to 1.0 R-4308.

b. Coating of Membrane substrates.

Broadly, the cationically charge modifying agents are coated onto a hydrophobic organic polymeric membrane by the following procedures: The hydrophobic membrane is first pre-wet in a water miscible organic solvent (i.e., alcohol) followed by exchange with water. This membrane is then coated by placing it in an aqueous solution of the charge modifying agent. Alternately, the process involves contacting the hydrophobic membrane substrate with an aqueous solution of a water miscible organic solvent (i.e., alcohol) which contains the charge modifying agent. The coating can be applied by dipping, slot coating, transfer rolling, spraying and the like. The coated membrane is then dried and cured under restraint. Suitable methods for drying and curing include the use of a heat transfer drum, hot air impingement, radiational heating or a combination of these methods.

Membranes to be coated (Immobilon P™, a hydrophilic poly-vinylidene fluoride, 0.45 micron pore size and Durapore™, a hydrophilic polyvinylidene fluoride, 0.65 micron pore size, both available from Millipore Corporation, Bedford, Mass. are preferred) 15.0×25.0 cm, are prewetted in isopropanol (IPA) and then exchanged in water. The samples are soaked in the 3% alkaline R-4308 solution for at least one hour and then air dried. The dry samples are then rewetted in IPA, exchanged in water and re-introduced into the R-4308 solution for 24–48 hours. The samples are then blotted to remove surface droplets and then dried in an oven at 75–90 deg. C. Suitable membranes tier this coating are made from PVDF, UPE, PP, PTPE, cellulosics, PVF, polysulfone and polyethersulfone among others. The best transfer of blots have been from membranes with high surface areas—BET of 10–25 m²/gm. Immobilon-N™ membranes are not prewetted with IPA. Also, no prewetting step is needed for a 2nd, optional coat.

c. Results.

Table 1 shows 3 membranes made according to this general process. The ratio of alkali to polymer is varied, and the solution pH after 24 hours is measured. In addition, 2 coats were used to make the preferred embodiment, the 61 c UPE membrane.

TABLE 1

| ALKALI LADDER SERIES (R-4308 COATINGS) | | | | |
|---|---|---|---|---|
| SAMPLE NO. | NaOH/ R-4308 | No. Coats | 24 Hr. pH | Comments |
| 58A (UPE) | 0.25/1 | 1 | 8.88 | Hercules stoichiometric point |
| 61C (UPE) | 0.1/1 | 2 | 7.32 | 2nd Coat 48 hr Soak |
| Immobilon N™ | 0.18/1 | 1 | 8.05 | Coat from 20% Solution in H2O |

The 24 hr. pH is selected to reflect the alkali effect; beyond 24 hours the pH change is slight. The pH of the freshly made solution undergoes rapid change over a 4 hour period, depending on the alkali level (note that R-4308 comes as an acidic solution with a pH of 4.0).

Example 2 - Epoxide Potential Assay

Using the uncharged fluorescent amine probe 2-aminoacridone (structure of AMAC shown in FIG. 5, panel A), a scale of reactive site density was established for surfaces with varying epoxide levels. Generally, decreasing reactive site density correlated with increasing amounts of alkali used to prepare and cross-link the surface.

a. Preparation of AMAC solution and epoxide potential assay.

A $10^{-4}$M solution of AMC was prepared by 1/10 dilution of a $10^{-3}$M AMAC stock solution in isopropanol with 0.1M NaOH; an inert polymer membrane was then immersed in the above solution and placed on top of the selected membranes under moderate pressure for one hour. After thorough washing in MilliQ™ water and air drying, the fluorescence spectrum of the reacted surface was recorded using a SLM/Aminco model SP-500 spectrophotofluorimeter fitted with a reflectance fluorescence attachment.

b. Results.

Table 2 gives the fluorescence density at 520 nm in arbitrary fluorescence emission units. Also included in the table is a column indicating the amount of alkali used in preparing the R-4308 surface as a ratio of solid NaOH to solid R-4308. The fluorescence units shown have been adjusted to account for the background fluorescence signal from the underlying substrate (0.45 micron PVDF) or 0.1 micron UPE coated with unreacted R-4308.

TABLE 2

| EPOXIDE POTENTIAL AS A FUNCTION OF ALKALI USED FOR CROSS-LINKING R-4308 ON VARIOUS MEMBRANES | | | |
|---|---|---|---|
| MEMBRANE | NaOH/ R-4308[1] | COMMENT | FLUORESCENCE[2] |
| UPE (73-1) | 10/1 | VERY LARGE EXCESS | 0 |
| UPE (59-c) | 0.5/1 | LARGE EXCESS | 0.4 |
| UPE (81-1) | 0.1M NaOH TREATED | AS IN IMMOBILIZATION | 1.4 |
| UPE (58-A) | .25/1 | HERCULES' EQUIV POINT | 1.5 |
| PVDF (INXA) | .18/1 | IMMOBILON-N | 2.3 |
| UPE (61-C) | .1/1 | UPE (PREFERRED) | 4.3 |
| UPE | .05/1 | 20% OF 58-A | 4.2 |

TABLE 2-continued

EPOXIDE POTENTIAL AS A FUNCTION OF
ALKALI USED FOR CROSS-LINKING R-4308
ON VARIOUS MEMBRANES

| MEM-BRANE | NaOH/R-4308[1] | COMMENT | FLUORES-CENCE[2] |
|---|---|---|---|
| (62-3) UPE (75-1) | 0/1 | E BEAM PRE-PARED[3] | 4.7 |

[1]As solid NaOH to solid R-4308 (w/w)
[2]Arbitrary fluorescence units (HV900, G100); values adjusted from emission from substrate
[3]No alkali used to cross-link R-4308

The data indicate a good correlation between reactive site density and the amount of alkali used in making the coating. The extremes are in stark contrast to each other, with commercially available Immobilon-N™ lying about the midway point. A ratio of 0.25/1 w/w is the stoichiometric point. Membrane (UPE) 61-C is prepared with a ratio of 0.1/1, and exhibits the best characteristics of the non-electron beam prepared membranes.

Maximization of the epoxide potential of the coated membrane is achieved by using no alkali and electron beam treatment or a stoichiometrically minimal amount of base such that epichlorohydrin content of the membrane is maximized.

Example 3-Wheat starch ladder covalent immobilization a. Preparation of ANTS-derivatized Wheat Starch Ladder The use of polyacrylamide-gel electrophoresis for analyzing saccharides labeled with the charged fluorophore 8-aminonaphthalene-1,3,6-trisulfonic acid is described in Jackson, Peter, *Biochem. J.* 270:705–713 (1990). Heat-hydrolyzed wheat starch (Sigma P/N S2760) was suspended, with vigorous mixing, at a concentration of 10 mg/ml in 0.1M ammonium acetate buffer, pH 5.5, at 37° C. To 50 μl of this suspension was added 5 μg of alpha-amylase/ml Boehringer-Mannhein P/N 161 764). The mixture was incubated at 37° C. for 30 minutes, after which time the digestion was stopped by the addition of 1 ml of ice-cold ethanol and dried under vacuum using a centrifugal vacuum evaporator. The digestion products (alpha 1–4 linked glucose oligomers) were allowed to react with ANTS under standard conditions.

b. Electrophoresis.

The ANTS labeled wheat starch hydrolysate mixture is subjected to polyacrylamide gel electrophoresis (per the N-Linked Oligosaccharide Profiling Kit, Millipore Corp. Part No. FACE-NOP-KT, Bedford, Mass.) resulting in the resolved fluorescent band pattern displayed in FIG. 6, panel A. The wheat starch hydrolysate is clearly resolved into a series of bands of increasing polymer size.

c. Transfer from the electrophoresis gel by contact blotting to a membrane substrate.

A piece of ultrahigh molecular weight polyethylene (UPE) treated with R-4308 as described in Example 1 was placed over the gel so as to be in good contact for a period of 2 hours. The UPE may be weighted down if necessary to provide good contact to ensure transfer of the images in the gel to the membrane. During this time the bands transfer from the gel to the membrane surface by passive diffusion (see FIG. 6, panel B) with no fluorescence remaining in the gel after transfer (panel C).

d. Covalent Immobilization.

At this point the membrane was cut in half to provide two samples. Both pieces are positioned on a flat surface. One piece is treated with a deionized water-filled membrane to act as a control. The membrane of choice is Millipore® hydrophilic Durapore®, which is simply dipped in deionized water and placed in close contact with the membrane containing the adsorbed ANTS-conjugates. The pair of membranes are sandwiched between two sheets of polyethylene film to reduce liquid loss by evaporation. The remaining half of the test membrane is treated identically, except that instead of deionized water, the hydrophilic Durapore is dipped into 0.1M sodium hydroxide.

e. Results.

After one hour, both membranes are separated and washed with water. Both control (FIG. 6, panel D) and test pieces (FIG. 6, panel E) showed the same fluorescent band pattern as they had before their respective treatments. Each membrane is then prewetted with methanol and placed in a 2% aqueous NaCl salt solution. Starting at this point, the control membrane displays gradually decreasing fluorescent intensity in its band pattern [See Table 3]. After 2 hours' residence time in the salt solution, much of the original fluorescence in the control membrane (FIG. 6, panel F) has disappeared. The test membrane, on the other hand, maintains its original fluorescent intensity (FIG. 6, panel G).

TABLE 3

| | Time in 2% NaCL (min | | | | |
|---|---|---|---|---|---|
| | 0 | 10 | 20 | 30 | 60 |
| | % of Remaining Fluorescence[1] | | | | |
| I-N CONTROL | 100 | 25 | 10 | 5 | 5 |
| I-N TEST | 100 | 95 | 90 | 90 | 90 |
| UPE CONTROL | 100 | 25 | 10 | 5 | 5 |
| UPE TEST | 100 | 95 | 90 | 90 | 90 |

[1]Derived from arbitrary fluorescence units as measured in Example 2.

The loss of fluorescence from the control membrane is due to desorption of the negatively charged ANTS-carbohydrate conjugates from the positively charged R-4308 polymer by neutralization and competition from excess competing choride ions. In the test sample, however, hydroxide treatment triggered the covalent reaction of the ANTS-carbohydrate conjugate with the expoxide moieties on the R-4308 polymer. This produced a covalent bond which is extremely stable to high salt and many other active chemical conditions. These results are shown in FIG. 6 displays the control (panel F) and test lanes (panel G) after being in the salt solution for 2 hours.

Example 4-Transfer of N-Acetylglucosamine Oligosaaccharides and Probing with Biotinylated Wheat Germ Lectin.

a. Materials

N-acetylglucosamine oligomers were obtained from the acid hydrolysis of crab shell chitin (Sigma Cat. No. C-3641) and were fractionareal according to the methodology of Barker, S. A., et al., *J. Chem. Soc.* 2218–2227 (1958). Oligosaccharide labeling reagents and electrophoresis gels and buffers were used from the N-linked Oligosaccharide Profiling Kit (FACE-NOP-KT, Millipore Corporation, Bedford, Mass.). The lectins and reagents for staining were used from the Lectin-Link Kit (LEKL, Genzyme Corporation, Cambridge, Mass.).

b. ANTS labeling.

A series of linear N-acetylglucosamine oligomers were conjugated to ANTS using the procedure outlined in Example 3.

The oligosaccharides (N-acetylglucosamine oligomers) were prepared as aqueous solutions at a concentration of 1 mg/ml. The N-acetylglucosamine oligomer solution (20 μl) was placed into a 0.5 ml microcentrifuge tube (Eppendorf) and taken to dryness in a centrifugal vacuum evaporator (SAVANT). To each tube, 5 μl of the oligo labeling dye (ANTS, 8 mg/125 μl of 15% acetic acid) and 5 μl of the labeling reducing agent (sodium cyanoborohydride, 8 mg/125 μl in dimethylsulfoxide) were added and incubated in a water bath at 37° C. for 16 hours according to the protocols specified in the N-Linked Oligosaccharide Profiling Kit (Millipore Corp. P/N FACE-NOP-KT). After 16 hours the samples were both reduced to a viscous liquid in a centrifugal vacuum evaporator at 20 mTorr with no heat applied, for 1 hour. Each sample was dissolved in Milli-Q® water (100 μl) and 2×loading buffer (100 μl, 25% aqueous glycerol). The loading volume per gel lane was 4 μl.

c. Electrophoresis.

The ANTS labeled N-acetylglucosamine oligomers are then subjected to polyacrylamide gel electrophoresis (per the N-Linked Oiigosaccharide Profiling Kit, Millipore Corp. Part No. FACE-NOP-KT, Bedford, Mass.) resulting in the resolved fluorescent band pattern corresponding to conjugated tetra-, penta-, hexa-, and heptamers displayed in FIG. 7, panel A.

Each of the samples were electrophoresed according to the protocols of the N-Linked Oligosaccharide Profiling Kit. Essentially, 4 μl of the individual samples were placed into each of the 8 wells of separate electrophoresis gels. The gel was placed into the Glycoscan™ Electrophoresis Gel Box, filled with the electrophoresis buffer (50 mM Tris/50 mM Tricine, pH 8.3). The gels were then electrophoresed in the Glycoscan™ Electrophoresis Unit for 1 hour 30 minutes at a constant 15 mA/gel at 4° C. After completion of the electrophoresis, the gels were removed, rinsed with Milli-Q® water and imaged with the Glycoscan™ Imager (Millipore Corp.)

d. Transfer from the electrophoresis gel by contact blotting to a membrane substrate.

A piece of ultrahigh molecular weight polyethylene (UPE) treated with R-4308 as described in Example 1 was placed over the gel so as to be in good contact for a period of 2 hours. The UPE may be weighted down if necessary to provide good contact to ensure transfer of the images in the gel to the membrane. During this time the bands transfer from the gel to the membrane surface by passive diffusion. A sample of nylon (Zetabind, Cuno, Meriden, Conn.) was included as a control for comparison but was not subjected to the following covalent immobilization step.

e. Covalent Immobilization.

At this point the membrane containing the ANTS labeled conjugates was activated by overlayering with a Millipore® hydrophilic Durapore® membrane filled with 0.1M sodium hydroxide. The pair of membranes are then sandwiched between two sheets of poly6thylene film to reduce liquid loss by evaporation.

f. Probing with Biotinylated Wheat Germ Lectin.

The membranes were probed using a commercial biotinylated lectin-based protocol. This experiment was essential to demonstrate that the immobilized carbohydrate remains chemically unaltered and resides in an environment allowing free and unencumbered access to the lectin molecule.

The N-acetylglucosamine oligomers were probed with biotinylated wheat germ lectin (Lectin-Link Kit, Genzyme Corp., Cambridge, Mass., P/N LEKL). The probing of the oligosaccharides used the protocol included in the Lectin-Link Kit. Essentially, each membrane was wet with methanol, rinsed with Milli-Q® water, and then placed into the blocking buffer for 1 hour.

The lectin probing of the membrane was as follows:
1. The membrane was wetted by immersion in methanol for 1 minute.
2. The wetted membrane was placed into Milli-Q™ water until the membrane sank.
3. The membrane was blocked by placing the membrane into the blocking buffer (Tris buffer, pH 7.4 with salts containing fish gelatin) for 60 minutes and gently rotated using a platform shaker.
4. The membrane was incubated for I hour in blocking buffer containing one of the biotinylated lectins ( wheat germ lectins, 40 μg/10 ml blocking buffer).
5. After the 1 hour incubation, the membrane was soaked with a wash buffer (Tween 20 in Tris buffer, pH 7.4 with salts) 3 times for 10 minutes each.
6. The membrane was incubated for 1 hour in the avidin-biotinylated alkaline phosphatase reagent for 1 hour.
7. The membrane was soaked in the wash buffer (Tween 20 in Tris buffer, pH 7.4 with salts) 3 times for 10 minutes each.
8. The membrane was rinsed with staining buffer (Tris buffer, pH 9.5 with salts).
9. The staining was pipetted solution (5-bromo-4-chloro-3-indolyl phosphate/nitroblue tetrazolium) over the membrane, colored bands were allowed to appear (10 minutes), then the membrane was immersed in water.
10. The membranes were air-dryed on a paper towel in the dark.

g. Image Analysis of Stained Blots.

The lectin-blotted membranes were imaged using the Bio Image low light camera system (Bio Image Model 110S-2D Electrophoresis Analyses, P/N BITS- 12S-2D, Millipore Corp., Bedford, Mass.)

h. Results.

Figure 7A:
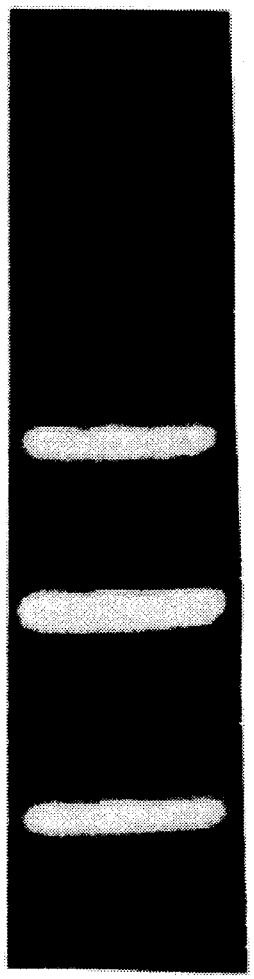
FIG. 7 panel A is a photograph of a gel containing a resolved fluorescent band pattern corresponding to conjugated tetra-, penta-, hexa-, and heptamers of N-acetylglucosamine oligomers. Panel B is a membrane (UPE-R4308 treated) displaying lectin binding to the full series of N-acetylglucosamine oligomers. The nylon membrane (Panel C), on the other hand, showed a very high background density with bands only weakly visible.
Figure 7B:
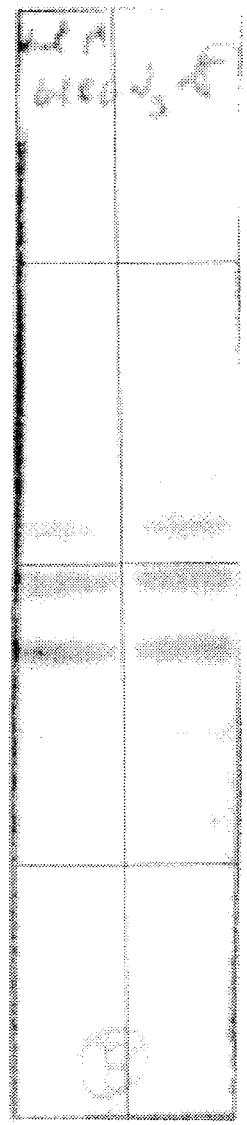
Figure 7C:
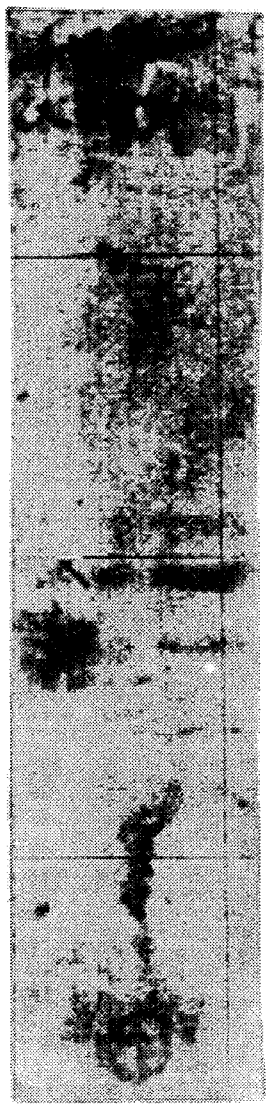

As can be seen, the UPE-R4308 treated membrane clearly displayed lectin binding to the full series of N-acetylglucosamine oligomers (see FIG. 7, panel B). The nylon membrane, on the other hand, showed a very high background density with bands only weakly visible (See FIG. 7, panel C). This result clearly illustrates the retention of the ANTS-glycan conjugates on the experimental membrane surface in a biologically active configuration. As shown by Panel C, the nylon substrate did not retain the ANTS-glycan conjugates quantitatively under the conditions of the lectin probing protocol. In contrast, the pattern of glycans retained in Panel B reflects the original sample. The high background staining was not unexpected as this substrate has a high protein binding capacity which is difficult to saturate during background blocking conditions.

Example 5 - Sequence Analysis of Covalently-Immobilized ANTS-Oligosaccharides.

Structural determination of oligosaccharides can be accomplished by the covalent immobilization of the oligosaccharide onto a membrane with subsequent enzymatic digestion analysis, as taught herein. For example, an oligosaccharide mixture derived from a suitable source is labeled with ANTS or other suitable charge-carrying compound, and then purified by HPLC, IC, CE or PAGE. In this example PAGE is used. Separated ANTS-oligosaccharides are collected directly onto a membrane having epoxide potential and the ANTS-oligosaccharide bands are blotted onto the membrane from the polyacrylamide gels. Covalent immobilization is then carried out as discussed throughout this application.

Figure 8:
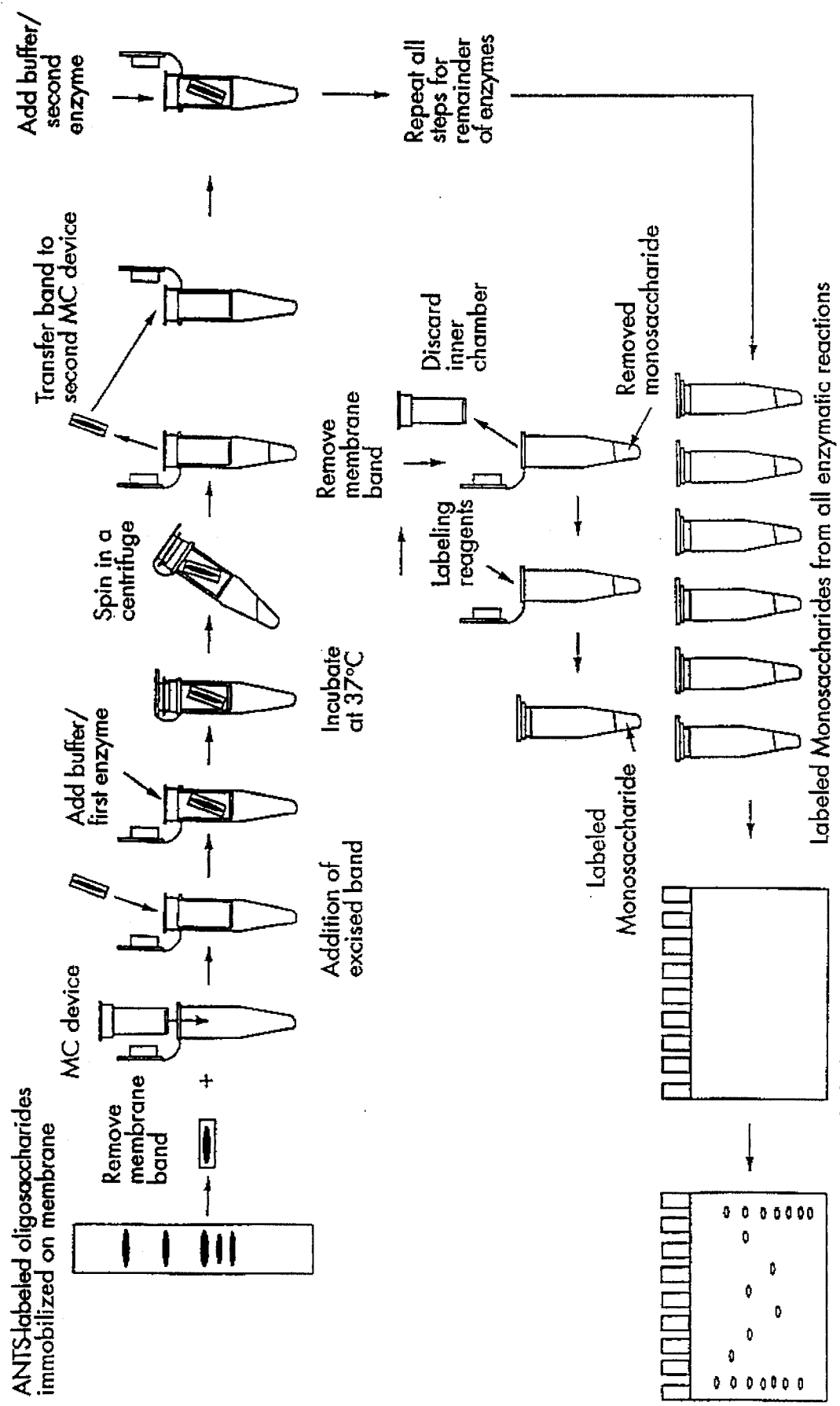
FIG. 8 is a pictograph of the use of this invention to sequence an oligosaccharide. Depicted are the membranes of this invention, Ultrafree™ reaction vessels, and PAGE analysis.

Once the ANTS-oligosaccharides are covalently attached, the membranes are cut into specific pieces containing the ANTS-oligosaccharide to be sequenced. With reference to FIG. 8, the membrane is then placed into a reaction vessel (Ultra-free,® Millipore Corp., Bedford, Mass.) having a 10K ultra filter membrane and the appropriate buffer containing the first enzyme (sialadase) is added. The enzyme is allowed to act upon the oligosaccharide, and for purposes of this example, sialic acid is clipped. After an appropriate time, the membrane is taken from the solution in the reaction chamber with tweezers, rinsed with water (which falls into the Ultra-free® chamber) and the membrane is transferred into a second Ultra-free® reaction chamber. (Because the membrane can be picked up physically, the researcher is guaranteed that the same amount of oligosaccharide is transferred into the second and subsequent reaction vessels for treatment with other enzymes.) The first Ultra-free® reaction chamber (containing the enzyme and the released monosaccharide) is placed into a centrifuge and spun to force the reaction solution through the membrane. Following centrifugation, the enzyme is retained by the membrane and the filtrate now contains the sialic acid. This monosaccharide is quantitatively analyzed by HPLC, IC, CE or PAGE. To the membrane which has been transferred to the second Ultra-free® reaction vessel, a new buffer system and the second enzyme is added and the process is repeated. Typical enzymes to be used include: sialidases, beta-galactosidase, beta-N-acetylhexosaminidase, alpha-mannosidase, beta-mannosidase and alpha-fucosidase.

A sequential exoglycosidase digestion is as follows:
1. Derivatize the oligosaccharide mixture with ANTS;
2. Electrophorese the labeled mixture on polyacrylamide gels to effect a separation and resolve the mixture into homogenous bands;
3. Transfer the oligosaccharide bands onto the membrane by blotting;
4. Carry out covalent immobilization as outlined in Example 3.
5. Visualize the bands using a low-wavelength UV light and scribe with a pencil the individual bands.
6. Carefully cut the individual bands out of the membrane (this will now be referred to as the "membrane band");
7. Wet the membrane band by immersing in methanol for 1 minute;
8. Place the wetted membrane band into water until the membrane sinks;
9. Transfer the membrane band into a disposable membrane-based centrifugal device such as a Ultrafree®-MC filter unit containing a polysulfone ultrafiltration membrane with a pore size of 10,000 (Millipore P/N UFC3 TGC 25), hereinafter "MC device";
10. Place approximately 50–100 μl of an appropriate buffer (such as 50 mM sodium phosphate, pH 6.0) into the upper chamber of the MC device containing the membrane band;
11. Add an appropriate amount of an enzyme specific for the removal of the terminal non-reducing sialic acids which may be present on the oligosaccharides immobilized on the membrane band. Such an enzyme may have a high specificity for a linkage [i.e. alpha 2-3,NANase I (Glyko P/N 80020), or alpha 2-3,8, Sialidase (Oxford GlycoSystems P/N X- 5017 or Neuraminidase (Genzyme Corporation P/N 2144–01 )] or a broad specificity of all linkages which possibly may exist [i.e. alpha 2-3,6,8, NANase III (Glyko P/N 80040), sialidase (Oxford Glycosystems P/N X-5016), Neuraminidase (Genzyme Corporation P/N NSS-1), Neuraminidase (Boehringer Mannhelm P/N's 107–590 and 1080–725) or Neuraminidase (New England Biolabs, Inc P/N 720S)];
12. Lower the cap of the MC device and incubate at 37° C. for approximately an hour;
13. Open the cap of the MC device and with a pair of tweezers pick up the membrane band. Rinse the membrane band with 20 to 50 ul of new buffer, with the buffer dropping into the upper chamber of the MC device;
14. Place the rinsed membrane band into a second MC device;
15. Replace the cap onto the first MC device and spin in a centrifuge at 2000 rpm for 1 hour or until the majority of the buffer has passed into the lower chamber of the MC device;
16. Place 50 μl of fresh buffer into the upper chamber of the first MC device, place back into the centrifuge and spin until the upper chamber is dry;
17. Open the cap of the first MC device, remove and discard the upper chamber, place the lower tube into a freezer until the solution is frozen and then lyophilize. Store this tube at 20° C. until all of the remaining enzymatic reactions are completed. At this time all the tubes will be derivatized;
18. From step 14, the membrane band in the second MC device can now be treated with either a broad specificity enzyme to remove any remaining sialic acid residues (repeating steps 10–17) or (if the membrane band was first treated with a broad specificity enzyme to remove all the sialic acid residues) an exo-beta-galactosidase;
19. To the second MC device containing the membrane band add 50 to 100 μl of an appropriate buffer (such as 20 mM sodium citrate/phosphate buffer, pH 3 to 6) for digestion with an exo-beta-galactosidase. This enzyme will remove non-reducing galactose residues;
20. Add an appropriate amount of the exo-beta-galactosidase to the second MC device [beta-Galactosidase (Oxford GlycoSystems P/N's X-5014,X-5013, X-5012, X-5008) and beta-Galactosidase (Boehringer Mannheim, P/N's 105–023, 903–345, 1088–718, 105–031)];
21. Close the lid of the MC device and incubate at 37° C.for 18–20 hours;
22. Repeat steps 13 through 17. Placing the membrane band into a third fresh MC device;
23. To the third MC device containing the membrane band add 50 to 100 μl of an appropriate buffer (such as 50 mM sodium citrate or sodium phosphate, pH 4.0 to 5.0) for digestion with an exo-N-acetyl-beta-D-hexosaminidase. This enzyme will remove non-reducing N-acetyl-beta-D-glucosamine and/or N-acetyl-beta-D-galactosamine residues;
24. Add an appropriate amount of the exo-N-acetyl-β-D-hexosaminidase to the third MC device (HEXase I (Glyko, Inc. P/N 80050), N-Acetyl-β-D Hexosaminidase (New England Biolabs, Inc. P/N 721-S), N-Acetyl-β-D Hexosaminidase ( Oxford GlycoSystems P/N X- 5003, X-5004 and X-5002), N-Acetyl-β-D Hexosaminidase (Boehringer Mannheim P/N 1017–098 and 1088–700)];
25. Close the lid of the MC device and incubate at 37° C. for 4 to 18 hours depending upon the manufacturer of the enzyme used;
26. Repeat steps 13 through 17. Place the membrane band into a fourth fresh MC device;
27. To the fourth MC device containing the membrane band add 50 to 100 μl of an appropriate buffer (such as 50 mM sodium phosphate or sodium acetate, pH 5.0 to 6.5) for digestion with an α-fucosidase. This enzyme is chosen to remove non-reducing terminal fucose residues;

28. Add an appropriate amount of the α-fucosidase to the fourth MC device [FUCase I (Glyko,Inc. P/N 80080), α-Fucosidase (Oxford GlycoSystems P/N's X-5005 and X-5006) and α-L-Fucosidase (Boehringer Mannheim P/N 104–949)];

29. Close the lid of the MC device and incubate at 37° C. for 18 hours;

30. Repeat steps 13 through 17. Place the membrane band into a fifth fresh MC device;

31. To the fifth MC device containing the membrane band add 50 to 100 µl of an appropriate buffer (such as 50 mM sodium phosphate or sodium acetate, pH 5.0 to 6.0) for digestion with an α-mannosidase. This enzyme is chosen to remove non-reducing terminal alpha-mannose residues;

32. Add an appropriate amount of the α-mannosidase to the fifth MC device [MANase I (Glyko,Inc. P/N 80060), α-Mannosidase (Oxford GlycoSystems P/N X-5010 and X-5009), and α-Mannosidase (Boehringer Mannheim P/N 107–379)];

33. Close the lid of the MC device and incubate at 37° C. for 18 hours;

34. Repeat steps 13 through 17. Placing the membrane band into a sixth fresh MC device. (At this point the only oligosaccharide structure remaining should have the structure: Mannose β1-4N-Acetylglucosamine α1-4N-acetylglucosamine.)

35. To the sixth MC device containing the membrane band add 50 to 100 µl of an appropriate buffer (such as 100 mM sodium acetate, pH 4.0) for digestion with an α-mannosidase. This enzyme is chosen to remove non-reducing terminal α-mannose residues.

36. Add an appropriate amount of the α-mannosidase to the sixth MC device [α-Mannosidase (Oxford GlycoSystems P/N X-5015)];

37. Close the lid of the MC device and incubate at 37° C. for 18 hours.

38. Repeat steps 13 through 17 (The membrane band consists only of two residues of N-Acetylglucosamine linked beta 1–4. No further enzymatic treatment will be necessary for structure determination.);

39. Remove all reaction tubes from the freezer. Each tube will possibly contain a monosaccharide for further analysis.

To determine the presence of the monosaccharide and to perform a quantitative monosaccharide analysis the contents of the tubes will be treated according to the instructions of the FACE Monosaccharide Composition Analysis Kit (Millipore P/N FACE MCA KT).

1. Reconstitute the monosaccharide labeling dye (2-aminoacridone, AMAC vial B4) (3 mg) in dimethylsulfoxide (75 µl). Reconstitute the labeling reducing agent (sodium cyanoborohydride, vial B1) (8 mg) in dimethlysulfoxide (125 µl);

2. Reconstitute the dried contents of each reaction tube in 2.5 µl of 30% aqueous acetic acid;

3. Add 2.5 µl of the monosaccharide labeling dye and 5.0 µl of the labeling reducing agent to each tube. Close the cap, vortex and centrifuge;

4. Incubate at 37° C. for 16 hours;

5. After incubation, open cap, place into a centrifugal vacuum evaporator for 15 minutes or until the sample reaches a viscous gel stage;

6. Resuspend the labeled monosaccharides in dimethylsulfoxide (5 µl);

7. Add 5 µl of water, vortex and centrifuge for 30 seconds;

8. Place a 2 µl aliquot of this mixture into a second tube and add 2 µl of the 2×loading buffer (25% glycerol in water with bromophenol blue dye indicator) to give 4 µl of a 1:1 dilution of sample in loading buffer;

9. Load each sample into a single well of a precast monosaccharide precast gel (Millipore FACE MCG 05). Load also one lane of the monosaccharide ladder standard (Millipore FACE MSS 01) which contains labeled N-acetylgalactosamine, N-acetylneuraminic acid, mannose, fucose, glucose, galactose and N-acetylglucosamine;

10. Electrophorese the gel at 20 mA per gel and 20 watts per gel at a maximum voltage of 1000 for 2 hours at a constant temperature of 10° C.;

11. After electrophoresis, place the gel into the Glycoscan scanner (Millipore GLYC IMO 01) and image the gel for 15 to 20 seconds.

Figure 9:
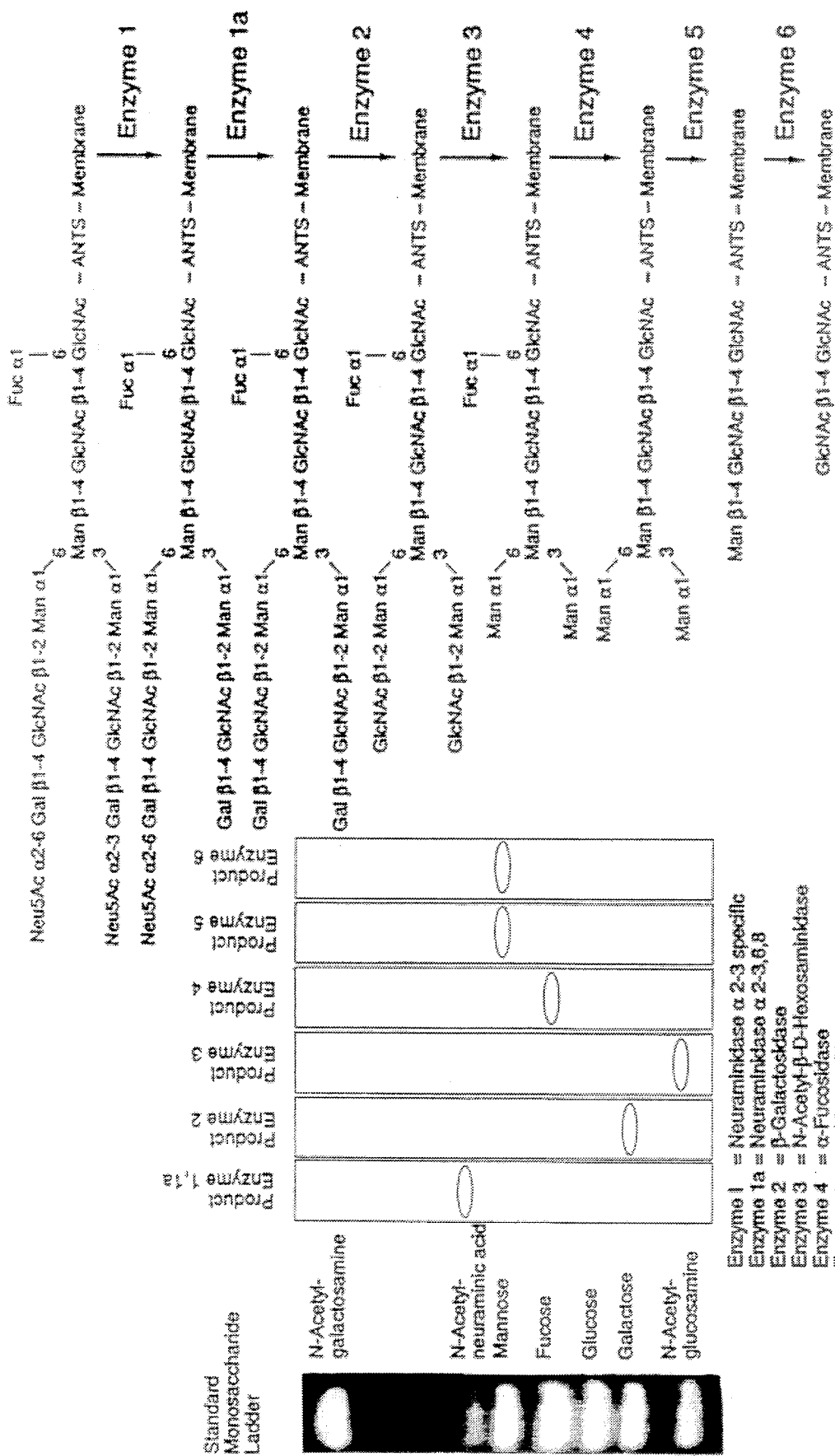
FIG. 9 is a standard monosaccharide ladder shown with prophetic gels depicting the expected pattern of monosaccharides released from complex glycan structures shown in the right portion of the Figure.

An example of the expected pattern of monosaccharides released from complex glycan structures is shown in FIG. 9. The retention of the ANTS-glycan conjugates on the membrane surface considerably simplifies this task. The right side of FIG. 9 shows the parent carbohydrate and subsequent daughters that decrease in size as a specific enzyme clips-terminal monosaccharides. The gels show where the expected monosaccharides would be, in relation to the standard Monosaccharide Ladder, shown at far left.

The invention has now been described by way of illustration and example for purposes of clarity and understanding, and it will be obvious that certain changes and modifications may be practiced within the scope of the invention, as limited only by the scope of the appended claims.

We claim:

1. A method for covalent immobilization of a charged carbohydrate conjugate with an oppositely charged surface, comprising the steps of:

(a) coating a microporous pelymeric base membrane with a cationic polyamido-polyamine epichlorohydrin polymer having fixed charges thereon;

(b) cross-linking said cationic polymer onto said polymeric base membrane by using less than a stoichiometric amount of base relative to the original epichlorohydrin content of said cationic polymer such that a composite membrane is formed which has sufficient epichlorohydrin and epoxide moieties remaining on the surface of said composite membrane for covalent immobilization of an oppositely-charged carbohydrate conjugate;

(c) adsorbing said charged carbohydrate conjugate to said composite membrane in proximity to said epichlorohydrin and epoxide moieties bound to said composite membrane and being capable of reacting with said charged carbohydrate conjugate; and (d) activating said bound moieties sufficiently for covalent attachment to said adsorbed charged carbohydrate conjugate.

2. The method of claim 1 wherein said charged carbohydrate conjugate comprises a negatively-charged amine covalently attached to a carbohydrate molecule.

3. The method of claim 2 wherein said negatively-charged amine comprises a fluorophore.

4. The method of claim 2 wherein said negatively-charged amine is selected from the class of sulfonated aminonaphthalenes.

5. The method of claim 1 wherein said carbohydrate molecule is selected from the group consisting of glycoproteins, proteoglycans, glycolipids, glycosphingolipids, polysaccharides, and glycosaminoglycans.

6. The method of claim 2 wherein said carbohydrate molecule is an ANTS-glycan conjugate.

7. The method of claim 1 wherein said composite membrane is polyethylene coated with said polyamido-polyamine epichlorohydrin cationic polymer.

8. The method of claim 1 wherein said composite membrane is polyvinylidene fluoride coated with said polyamido-polyamine epichlorohydrin cationic polymer.

9. The method of claim 1 wherein said composite membrane is polytetrafluoroethylene coated with said polyamido-polyamine epichlorohydrin cationic polymer.

10. The method of claim 1 wherein adsorbing said charged carbohydrate conjugate to said composite membrane comprises transferring said charged carbohydrate conjugate from a gel onto the surface of said composite membrane.

11. The method of claim 1 wherein activating said epichlorohydrin moiety sufficiently for covalent attachment to said absorbed charged carbohydrate conjugate comprises contacting said composite membrane with a base.

12. The method of claim 1 wherein activating said epichlorohydrin and epoxide moieties sufficiently for covalent attachment to said adsorbed charged carbohydrate conjugate comprises raising the temperature of said composite membrane so that covalent attachment occurs.

13. The method of claim 1 wherein said polymeric base membrane is selected from the group consisting of polyvinylidene fluoride, polyethylene, polypropylene, polymethylmethacrylate, polymethacrylate, polysulfone, polyethersulfone, polyfluoroethylene and polytetrafluoroethylene.

14. A method for covalent immobilization of a carbohydrate molecule with an oppositely charged surface, comprising the steps of:
   (a) conjugating a carbohydrate mixture with a negatively-charged aminofluorophore to form a mixture of derivatized conjugates;
   (b) separating said derivatized conjugates from each other by gel electrophoresis;
   (c) transferring said derivatized conjugates from said gel onto a hydrophobic microporous polymeric base membrane coated with a cross-linked, cationic polymer having fixed charges thereon to form a composite membrane, said coating having sufficient epichlorohydrin and epoxide moieties for covalent immobilization of an oppositely-charged carbohydrate conjugate and being formed by using less than a stoichiometric amount of base relative to the original epichlorohydrin content during formation of said composite membrane; and
   (d) activating said epichlorohydrin and epoxide moieties sufficiently for covalent attachment of said oppositely-charged carbohydrate conjugate to said charged surface.

15. The method of claim 14 wherein said negatively-charged aminoflurophore is selected from the class of sulfonated aminonaphthalenes.

16. The method of claim 14 wherein said derivatized conjugates include a negatively-charged amine comprising ANTS (8-aminonaphthalene-1,3,6-trisulphonic acid).

17. The method of claim 14 wherein transfer of said derivatized conjugates from said gel to said membrane is by blotting.

18. The method of claim 14 wherein said oppositely-charged surface is polyethylene coated with a polyamido-polyamine epichlorohydrin cationic resin.

19. The method of claim 14 wherein said oppositely-charged surface is polytetrafluoroethylene coated with a polyamido-polyamine epichlorohydrin cationic resin.

20. The method of claim 14 wherein said oppositely-charged surface is polyvinylidene fluoride coated with a polyamido-polyamine epichlorohydrin cationic resin.

21. The method of claim 14 wherein activating said epichlorohydrin moiety comprises placing a sheet of strong-base-containing absorbent material in liquid communication with said composite membrane.

22. The method of claim 14 wherein activating said epichlorohydrin and epoxide moieties comprises raising the temperature of said composite membrane so that covalent attachment occurs.

23. The method of claim 21 wherein said base is selected from the group consisting of ammonium hydroxide and sodium hydroxide.

24. The method of claim 14 wherein said polymeric base membrane is selected from the group consisting of polyvinylidene fluoride, polyethylene, polypropylene, polymethylmethacrylate, polymethacrylate, polysulfone, polyethersulfone, polyfluoroethylene and polytetrafluoroethylene.

25. A hydrophobic composite membrane comprising a microporous polymeric base membrane and a coating of cationic polymer having fixed charges thereon bound to said membrane, said coating having sufficient epichlorohydrin and epoxide moieties remaining on its surface to enable covalent immobilization of an oppositely-charged carbohydrate conjugate to said membrane said composite membrane being formed by using less than a stoichiometric amount of base relative to the original epichlorohydrin content of said cationic polymer.

26. The composite membrane of claim 25 wherein said polymeric base membrane is selected from the group consisting of polyvinylidene fluoride, polyethylene, polypropylene, polymethylmethacrylate, polymethacrylate, polysulfone, polyethersulfone, PFA, and polytetrafluoroethylene.

27. The composite membrane of claim 25 wherein said polymeric base membrane comprises polyethylene coated with a polyamido-polyamine epichlorohydrin cationic resin.

28. The composite membrane of claim 25 wherein said polymeric base membrane comprises polyvinylidene fluoride coated with a polyamido-polyamine epichlorohydrin cationic resin.

29. The composite membrane of claim 25 wherein said polymeric base membrane comprises polytetrafluoroethylene coated with a polyamido-polyamine epichlorohydrin cationic resin.

30. A method for preparing the composite membrane of claim 25 comprising the steps of:
   (a) contacting said hydrophobic microporous polymeric base membrane with an alkaline solution of a polyamido-polyamine epichlorohydrin polymer, said solution having less than a stoichiometric amount of alkaline agent relative to the original epichlorohydrin content of said cationic polymer to enhance the epoxide potential of said composite membrane;
   (b) crosslinking said polymer onto the surface of the membrane; and
   (c) curing said membrane 31. The method of claim 30 wherein the ratio of base to 20% polyamido-polamine epichlorohydrin cationic resin aqueous solution is from about 0.20/1.0 to about 0.05/1.0 on a weight-to-weight basis.

* * * * *